United States Patent [19]

Sato et al.

[11] 4,220,755

[45] Sep. 2, 1980

[54] FORTIMICIN B DERIVATIVES AND PROCESS FOR PRODUCTION THEREOF

[75] Inventors: Moriyuki Sato, Machida; Yasuki Mori, Kawasaki, both of Japan

[73] Assignee: Abbott Laboratories, North Chicago, Ill.

[21] Appl. No.: 836,229

[22] Filed: Sep. 23, 1977

[30] Foreign Application Priority Data

Sep. 23, 1976 [JP] Japan .................................. 51-114306

[51] Int. Cl.$^2$ ............................................. C07H 15/22
[52] U.S. Cl. .................................. 536/17 R; 424/180; 536/4
[58] Field of Search .................................... 536/10, 17

[56] References Cited

U.S. PATENT DOCUMENTS

| 3,350,387 | 10/1967 | Vanderhaeghe | 536/10 |
| 3,925,353 | 12/1975 | Umezawa et al. | 536/17 |
| 3,976,768 | 8/1976 | Nara et al. | 424/118 |
| 3,997,524 | 12/1976 | Nagabhushan | 536/17 |
| 4,044,123 | 8/1977 | Daniels et al. | 536/17 |
| 4,048,430 | 9/1977 | Cooper et al. | 536/17 |
| 4,063,015 | 12/1977 | Mallams | 536/17 |

Primary Examiner—Johnnie R. Brown
Attorney, Agent, or Firm—Fitzpatrick, Cella, Harper & Scinto

[57] ABSTRACT

The present invention relates to certain novel 4-N-substituted derivatives of the antibiotic Fortimicin B and processes for production thereof. Included in the process aspect of the invention, is a novel method for the semi-synthetic production of the antibiotic Fortimicin C.

51 Claims, No Drawings

FORTIMICIN B DERIVATIVES AND PROCESS FOR PRODUCTION THEREOF

BACKGROUND OF THE INVENTION

The present invention relates generally to 4-N-substituted derivatives of fortimicin B, their pharmaceutically acceptable acid addition salts, and a process for producing the same, as well as novel synthetic processes for producing the compounds fortimicin A and fortimicin C.

Fortimicins (A, B and C) are compounds classified as pseudodisaccharides containing 1,4-diaminocyclitol. The physical properties and antibacterial activities of these compounds and processes for production thereof by fermentation are described in U.S. Pat. Nos. 3,931,400, 3,976,768, and 4,048,015, which descriptions are incorporated herein.

The planar structural formulae of the known fortimicins are shown in the above-mentioned United States specifications. As a result of further studies, it has been found that the structural formulae of fortimicin B, fortimicin A and fortimicin C are given by the following formulae:

Fortimicin B
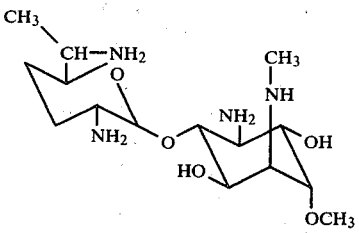

Fortimicin A
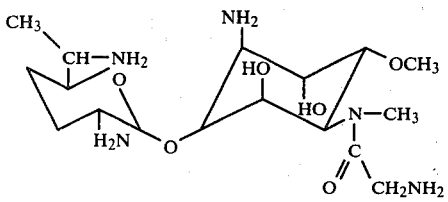

Fortimicin C
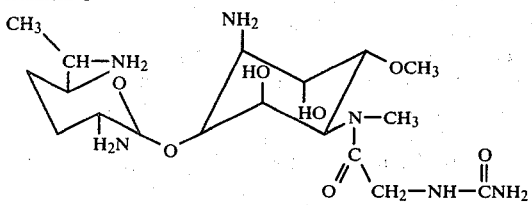

Structures of fortimicins A, B and C are described below:

(1) Fortimicin B

Results of mass spectrum of fortimicin B are given below:

m/e 349(M+ +1), 348(M+), 331, 313, 305, 235, 217, 207, 143, 126.

It is presumed from the results of the mass spectrum that fortimicin B has the following partial structural formula containing purpurosamine B.

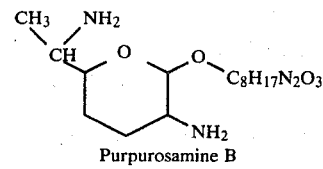
Purpurosamine B

The results from the analysis of PMR spectrum and CMR spectrum of fortimicin B in deuterium oxide are given below:

| PMR | δ (ppm) | Internal standard | DSS |
|---|---|---|---|
| H-1' | 5.03 | H-1 | 2.96 |
| H-2' | ~2.9 | H-2 | 3.68 |
| CH$_2$-3',4' | 1.2–1.9 | H-3 | 3.62 |
| H-5' | ~3.6 | H-4 | 3.06 |
| H-6' | 2.80 | H-5 | 3.96 |
| CH$_3$-6' | 1.00 | H-6 | 3.42 |
| | | OCH$_3$ | 3.42 |
| | | NCH$_3$ | 2.36 |
| J$_{1',2'}$ | 3.8 | J$_{1',2}$ | 9.5 |
| J$_{5',6'}$ | 7 | J$_{2',3}$ | ~3 |
| | | J$_{3',4}$ | 3 |
| | | J$_{4',5}$ | 4.5 |
| | | J$_{5',6}$ | 9.5 |
| | | J$_{1',6}$ | 9.5 |

| CMR | δ (ppm) | Internal standard | Dioxane (67.4 ppm) |
|---|---|---|---|
| C-1' | 102.4 | C-1 | 53.8 |
| 2' | 50.6 | 2 | 71.1 |
| 3' | 27.1 | 3 | 79.9 |
| 4' | 27.4 | 4 | 60.8 |
| 5' | 75.1 | 5 | 71.1 |
| 6' | 50.4 | 6 | 84.1 |
| 6'-CH$_3$ | 18.7 | OCH$_3$ | 59.3 |
| | | NCH$_3$ | 36.0 |

From these data of PMR and CMR, and spectrophotometric data of copper complexes of fortimicin B, diethylthioacetal derivative of purpurosamine B portion, and methyl glycoside derivative prepared according to the conventional processes, the absolute structure of fortimicin B has been determined to be:

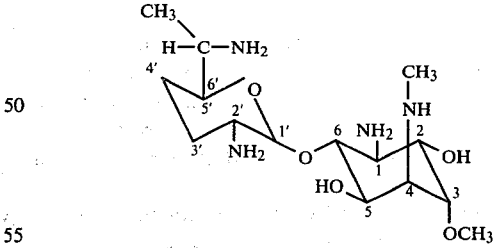

Other physical data of fortimicin B are:
m.p. 101°–103° C.
$[\alpha]_D^{23°} = +30.3°$ (c=1.0, water).
Elemental analysis as $C_{15}H_{32}N_4O_5 \cdot H_2O$; Calculated: C, 49.15; H, 8.80; N, 15.29; Found: C, 49.36; H, 8.77; N, 15.38.

(2) Fortimicin A

Mass spectrum: m/e 406(M+ +1), 405(M+), 388, 370, 362, 292, 274, 263, 246, 143, 126.

PMR (deuterium oxide): δ(ppm), 1.06(3H,d), 1.2–1.9(4H,m), ~2.8(1H,br), 2.86(1H,m), 3.05(3H,s), 3.44(3H,s), ~3.5(2H,br), 3.52(2H,s), 3.88(1H,q), 4.08(1H,q), 4.16(1H,t), 4.36(1H,t), 4.84(1H,d), 4.95(1H,q).

CMR (deuterium oxide): δ(ppm), 18.7, 27.1, 27.3, 32.3, 41.6, 50.2, 50.5, 52.5, 55.0, 56.4, 71.1, 73.0, 73.6, 75.1, 78.4, 100.1, 169.5.

Other physical data of fortimicin A are:
m.p.: above 200° C.(dec.).
$[\alpha]_D^{25°} = +26.0°$ (c=0.2, water).

Elementary analysis as $C_{17}H_{35}N_5O_6$; Calculated: C, 50.35; H, 8.70; N, 17.27; Found: C, 50.23; H, 8.67; N, 17.49.

From the foregoing data, and the fact that hydrolysis of fortimicin A produces fortimicin B and glycine, the structure of fortimicin A has been confirmed to be 4-N-glycylfortimicin B (Ia).

(3) Fortimicin C
Field desorption (FD) mass spectrum*: m/e 449($M^+ + 1$).
Mass spectrum**: m/e 406, 387, 375, 325, 292, 274, 264, 246, 235, 228, 217, 207, 200, 143.

* Mass spectrum where $M^+$ is liable to appear.
** $M^+$ fails to appear in ordinary mass spectrum (EI mass spectrum)

PMR (deuterium oxide): δ(ppm), 1.08(3H,d), 1.2–1.9(4H,m), ~2.8(1H,br), 2.85(1H,m), 3.10(3H,s), 3.43(3H,s), ~3.5(2H,br), 3.87(1H,q), 4.00 and 4.04 (jointly 2H, individually s), 4.07(1H,q), 4.18(1H,t), 4.38(1H,t), 4.84(1H,d), 4.92(1H,q)

CMR (deuterium oxide): δ(ppm), 17.5, 26.3, 27.5, 32.5, 44.1, 50.0, 51.1, 52.7, 55.5, 56.4, 71.0, 72.7, 73.1, 73.4, 77.9, 99.1, 161.7, 172.7

Other physical data of fortimicin C are given below:
m.p.: 153°–157° C.(dec.).
$[\alpha]_D = +84.3°$ (c=0.1, water).

Elementary analysis as $C_{18}H_{36}N_6O_7 \cdot 2H_2O$; Calculated: C, 45.00; H, 8.33; N, 17.50; Found: C, 44.84; H, 8.19; N, 17.36.

From the foregoing data, and a fact that hydrolysis of fortimicin C produces fortimicin B and hydantoic acid, the structure of fortimicin C has been found to be 4-N-hydantoyl fortimicin B (IIb) (fortimicins A and C have been synthetically derived from fortimicin B as given in Examples, and then the structures have been confirmed).

Fortimicins (A, B and C) all have antibacterial activity, but the antibacterial activity of B is not as good as the other factors; and A and C are slightly unstable under strongly alkaline conditions. Therefore, compounds having more distinguished properties are in demand.

As a result of various studies, the present inventors have found that certain 4-N-substituted derivatives of fortimicin B have enhanced antibacterial activity and good stability even under strongly alkaline conditions. Furthermore, the 4-N-alkyl-fortimicin B derivatives can be used as starting materials for further modified derivatives, i.e. introduction of other group(s) to the amino or hydroxy group(s) thereof.

DETAILED DESCRIPTION OF THE INVENTION

Compounds of the present invention are 4-N-substituted derivatives of fortimicin B represented by the general formula (I):

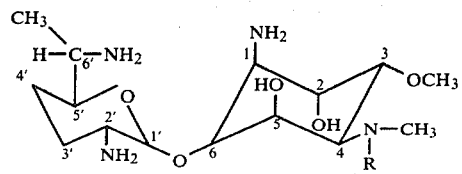

[wherein R shows a group represented by

or $-CH_2-R_2$, wherein $R_1$ represents an alkyl group having 2 to 8 carbon atoms, a hydroxyalkyl group having 1 to 5 carbon atoms, an aminoalkyl group having 2 to 8 carbon atoms, a carbamoxylaminoalkyl group having 3 to 9 carbon atoms, $R_2$ represents an alkyl group having 1 to 8 carbon atoms, a hydroxyalkyl group having 1 to 5 carbon atoms, an aminoalkyl group having 1 to 8 carbon atoms, a carbamoylaminoalkyl group having 2 to 9 carbon atoms, an N-alkylaminoalkyl group having 2 to 10 carbon atoms, an aminohydroxylalkyl group having 2 to 8 carbon atoms, an N-substituted aminoalkyl group (where the aminoalkyl group has 2 to 5 carbon atoms, and the N-substituents is an aminoalkyl group having 1 to 5 carbon atoms), or an N-alkylaminohydroxyalkyl group having 2 to 8 carbon atoms], and their pharmaceutically acceptable non-toxic acid addition salts.

4-N-substituted derivatives of fortimicin B derived from the compound represented by the general formula (IV), i.e. the compounds of the present invention, are exemplified in the following Table 1 together with their physical values. For reference, the physical properties of fortimicins B and A are also given.

In Table 2, the Rf values of thin layer chromatography (TLC) of these compounds developed on a silica gel plate using various solvents are shown. For a developed layer, a silica gel plate (Merck DC-Fertigplatten Kieselgel 60 F 254) was used, and colored with ninhydrin or iodine. The solvent system given in the table is as follows:

A: isopropanol-28% aqua ammonia-chloroform (2:1:1 by volume).
B: methanol: chloroform (5:95 by volume).
C: methanol: chloroform (1:9 by volume).

The antibacterial activity (MIC) of the compounds of the invention are shown in Tables 3-1 and 3-2. Measurement was carried out according to the agar dilution method, using a medium of pH 8.0, or the Japanese Antibiotic Medicament Standard, using a medium of pH 7.2 Units are in mcg/ml.

Microorganisms used in Table 3-2 and their abbreviations are given below:
S.A.: *Staphylococcus aureus* KY4279 ATCC6538P
B.S.: *Bacillus subtilis* KY4273
E.C.: *Eschericia coli* KY4271 ATCC26
P.V.: *Proteus vulgaris* KY4277 ATCC6897
S.S.: *Shigella sonnei* KY4281 ATCC9290
S.T.: *Salmonella typhosa* KY4278 ATCC9992
K.P.: *Klebsiella pneumoniae* KY4275 ATCC10031.

The identifying numbers of the compounds in Tables 3-1 and 3-2 are the same as in Table 1.

The stability of 4-N-acylfortimicin B derivatives in aqueous alkaline conditions is poor. For example, if fortimicin A free base was left standing in an aqueous solution (pH 10) at room temperature for 2 weeks or at 100° C. for 4 hours, it would be almost completely decomposed. If 4-N-(γ-Amino-α-hydroxybutyryl) fortimicin B and 4-N-(δ-amino-n-valeryl)fortimicin B were left standing in aqueous solutions (pH 10), these were almost completely decomposed within one hour at room temperature. Therefore, purification of these compounds under basic conditions (for example, column chromatography with Amberlite CG-50, eluting with aqueous ammonia) is not practical.

In contrast with the instability of 4-N-acylfortimicin B derivatives, 4-N-alkylfortimicin B derivatives are so stable that no decomposition occurs even in aqueous barium hydroxide solution at reflux temperature for 18 hours. Therefore, in the case of 4-N-alkylfortimicin B, any substituents can be introduced at 4-N-position of fortimicin B, even though such substituents can not be introduced as the acyl type to such position due to the aforementioned instability.

Table 1

| Compound Number | R in general formula (I) | Compound Name | Elemental analysis (%) Upper row: Calculated Lower row: Found | $[\alpha]_D$ of sulfate *1: 23° C. *2: 25° C. *3: 24° C. |
|---|---|---|---|---|
| 1 | H | fortimicin B | as $C_{15}H_{32}N_4O_5 \cdot H_2O$<br>C 49.15  H 8.80  N 15.29<br>49.36  8.77  15.38 | Note (1) *1<br>+30.3°<br>(c=1.0, water) |
| 2 | $-\underset{\underset{O}{\|\|}}{C}-CH_2-NH_2$ | fortimicin A | as $C_{17}H_{35}N_5O_6$<br>C 50.35  H 8.70  N 17.27<br>50.23  8.67  17.49 | Note (1) *2<br>+26.0°<br>(c=0.2, water) |
| 3 | $-\underset{\underset{O}{\|\|}}{C}-CH_2-NH-CONH_2$ | fortimicin C | as $C_{18}H_{36}N_6O_7 \cdot 2H_2O$<br>C 45.00  H 8.33  N 17.50<br>44.84  8.19  17.36 | Note (1) *2<br>+84.3°<br>(c=0.1, water) |
| 4 | $-\underset{\underset{O}{\|\|}}{C}-CH_2-OH$ | 4-N-glycolyl-fortimicin B | as $C_{17}H_{34}N_4O_7 \cdot 1.5H_2SO_4 \cdot C_2H_5OH \cdot H_2O$<br>C 36.95  H 7.34  N 9.07<br>36.70  7.44  8.93 | *1<br>+89.3°<br>(c=1.0, water) |
| 5 | $-\underset{\underset{O}{\|\|}}{C}-CH_3$ | 4-N-acetyl-fortimicin B | — | *2<br>+139.2°<br>(c=1.0, water) |
| 6 | $-\underset{\underset{O}{\|\|}}{C}-CH_2-CH_3$ | 4-N-propionyl-fortimicin B | — | *2<br>+136.8°<br>(c=1.0, water) |
| 7 | $-\underset{\underset{O}{\|\|}}{C}-CH_2-CH_2-CH_3$ | 4-N-(n-butyryl)-fortimicin B | — | *2<br>+131.0°<br>(c=1.0, water) |
| 8 | $-\underset{\underset{O}{\|\|}}{C}-(CH_2)_3-CH_3$ | 4-N-(n-valeryl)-fortimicin B | — | *2<br>+116.3°<br>(c=1.0, water) |
| 9 | $-\underset{\underset{O}{\|\|}}{C}-CH_2-CH_2-NH_2$ | 4-N-(β-alanyl)-fortimicin B | as $C_{18}H_{37}N_5O_6 \cdot 2H_2SO_4 \cdot C_2H_5OH \cdot 2.5H_2O$<br>C 33.14  H 7.51  N 9.66<br>32.96  7.41  9.71 | *1<br>+80.6°<br>(c=1.0, water) |
| 10 | $-\underset{\underset{O}{\|\|}}{C}-(CH_2)_3-NH_2$ | 4-N-(γ-amino-n-butyl)fortimicin B | as $C_{19}H_{39}N_5O_6 \cdot 2H_2SO_4 \cdot C_2H_5OH \cdot 4H_2O$<br>C 33.73  H 7.68  N 9.36<br>33.66  7.44  9.30 | *1<br>+81.8°<br>(c=1.0, water) |
| 11 | $-\underset{\underset{O}{\|\|}}{C}-(CH_2)_4-NH_2$ | 4-N-(δ-amino-n-valeryl)fortimicin B | — | *1<br>+89.5°<br>(c=1.0, water)<br>Only in this case, measured as hydrochloride |
| 12 | $-\underset{\underset{O}{\|\|}}{C}-(CH_2)_5-NH_2$ | 4-N-(ε-amino-n-caproyl)fortimicin B | as $C_{21}H_{43}N_5O_6 \cdot 2H_2SO_4 \cdot C_2H_5OH \cdot 2H_2O$<br>C 37.34  H 7.76  N 9.47<br>37.20  7.62  9.45 | *1<br>+74.9°<br>(c=1.0, water) |
| 13 | $-\underset{\underset{O}{\|\|}}{C}-CH_2-NH-\underset{\underset{O}{\|\|}}{C}-CH_2NH_2$ | 4-N-gylcylglycyl-fortimicin B | as $C_{19}H_{38}N_6O_7 \cdot 2H_2SO_4 \cdot C_2H_5OH \cdot 2H_2O$<br>C 33.24  H 7.17  N 11.07<br>33.27  7.11  10.81 | *2<br>+70.1°<br>(c=1.0, water) |
| 14 | $-\underset{\underset{O}{\|\|}}{C}-\underset{\underset{OH}{\|}}{CH}-CH_2-CH_2-NH_2$ | 4-N-[L-(−)-γ-amino-α-hydroxy-butyryl]fortimicin B | — | — |
| 15 | $-CH_2-CH_2-NH_2$ | 4-N-(2-aminoethyl)-fortimicin B | as $C_{17}H_{37}N_5O_5 \cdot 2.5H_2SO_4 \cdot C_2H_5OH \cdot H_2O$<br>C 32.56  H 7.21  N 9.99<br>32.55  7.19  9.93 | *2<br>+77.8°<br>(c=1.0, water) |
| 16 | $-CH_2-CH_3$ | 4-N-ethyl-fortimicin B | — | — |
| 17 | $-CH_2-CH_2-CH_3$ | 4-N-(n-propyl)-fortimicin B | — | — |
| 18 | $-(CH_2)_3-CH_3$ | 4-N-(n-butyl)- | | |

Table 1-continued

| Compound Number | R in general formula (I) | Compound Name | Elemental analysis (%) Upper row: Calculated Lower row: Found | $[\alpha]_D$ of sulfate *1: 23° C. *2: 25° C. *3: 24° C. |
|---|---|---|---|---|
| 19 | $-(CH_2)_4-CH_3$ | 4-N-(n-pentyl)-fortimicin B | — | — |
| 20 | $-(CH_2)_3-NH_2$ | 4-N-(3-aminopropyl)-fortimicin B | as $C_{18}H_{39}N_5O_5 \cdot 2 \cdot 5H_2SO_4 \cdot C_2H_5OH \cdot 2H_2O$<br>C 31.99 H 7.52 N 9.33<br>32.04  7.80  8.99 | *1<br>+71.9°<br>(c=1.0, water) |
| 21 | $-(CH_2)_4-NH_2$ | 4-N-(4-aminobutyl)-fortimicin B | as $C_{19}H_{41}N_5O_5 \cdot 2 \cdot 5H_2SO_4 \cdot C_2H_5OH \cdot 3H_2O$<br>C 32.98 H 7.64 N 9.16<br>32.74  7.69  8.91 | *1<br>+72.8°<br>(c=1.0, water) |
| 22 | $-(CH_2)_5-NH_2$ | 4-N-(5-aminopentyl)-fortimicin B | — | *1<br>+67.3°<br>(c=1.0, water) |
| 23 | $-(CH_2)_6-NH_2$ | 4-N-(6-aminohexyl)-fortimicin B | as $C_{21}H_{45}N_5O_5 \cdot 2 \cdot 5H_2SO_4 \cdot C_2H_5OH \cdot 2H_2O$<br>C 35.65 H 7.80 N 9.04<br>35.74  7.77  8.78 | *1<br>+71.3°<br>(c=1.0, water) |
| 24 | $-CH_2-CH_2-OH$ | 4-N-(2-hydroxyethyl)-fortimicin B | — | *3<br>+77.4°<br>(c=1.0, water) |
| 25 | $-CH_2-CH_2-NH-(CH_2)_2NH_2$ | 4-N-[2-(2-aminoethyl)aminoethyl]-fortimicin B | — | — |
| 26 | $-CH_2-CH_2-NHCH_3$ | 4-N-(2-methylaminoethyl)-fortimicin B | — | *2<br>+68.0°<br>(c=1.0, water) |
| 27 | $-CH_2-CH(OH)-(CH_2)_2NH_2$ | 4-N-[(S)-4-amino-2-hydroxybutyl]-fortimicin B | as $C_{19}H_{41}N_5O_6 \cdot 2 \cdot 5H_2SO_4 \cdot C_2H_5OH \cdot 3H_2O$<br>C 32.30 H 7.49 N 8.97<br>32.62  7.84  8.64 | *1<br>+78.6°<br>(c=1.0, water) |
| 28 | $-CH_2-CH(OH)-(CH_2)_2NHCH_3$ | 4-N-[(S)-4-methylamino-2-hydroxybutyl]-fortimicin B | as $C_{20}H_{43}N_5O_6 \cdot 2 \cdot 5H_2SO_4 \cdot C_2H_5OH \cdot H_2O$<br>C 34.65 H 7.65 N 8.93<br>34.82  7.44  9.22 | *1<br>+77.5°<br>(c=1.0, water) |
| 29 | $-CH_2-CH(OH)-(CH_2)_2-NH_2$ | 4-N-[(R,S)-4-amino-2-hydroxybutyl]-fortimicin B | as $C_{19}H_{41}N_5O_6 \cdot 2 \cdot 5H_2SO_4 \cdot C_2H_5OH \cdot 4H_2O$<br>C 31.57 H 7.57 N 8.76<br>31.44  7.98  8.48 | *3<br>+92.5°<br>(c=0.2, water) |
| 30 | $-CH_2-CH(OH)-(CH_2)_2-NHCH_3$ | 4-N-[(R,S)-4-methylamino-2-hydroxybutyl]-fortimicin B | — | — |
| 31 | $-CH_2-CH(OH)-CH_2-NH_2$ | 4-N-[(S)-3-amino-2-hydroxybutyl]-fortimicin B | as $C_{18}H_{39}N_5O_6 \cdot 2 \cdot 5H_2SO_4 \cdot C_2H_5OH \cdot H_2O$<br>C 32.87 H 7.17 N 9.58<br>32.85  6.93  9.23 | *1<br>+86.5°<br>(c=0.2, water) |
| 32 | $-CH_2-CH(OH)-CH_2-NHCH_3$ | 4-N-[(S)-3-methylamino-2-hydroxypropyl]-fortimicin B | as $C_{19}H_{41}N_5O_6 \cdot 2 \cdot 5H_2SO_4 \cdot C_2H_5OH \cdot 3H_2O$<br>C 32.30 H 7.49 N 8.97<br>32.48  7.40  8.71 | *1<br>+74.5°<br>(c=0.2, water) |
| 33 | $-CH_2-CH(OH)-(CH_2)_3NH_2$ | 4-N-[(S)-5-amino-2-hydroxypentyl]-fortimicin B | as $C_{20}H_{43}N_5O_6 \cdot 2 \cdot 5H_2SO_4 \cdot C_2H_5OH \cdot H_2O$<br>C 34.82 H 7.44 N 9.22<br>34.78  7.72  8.98 | *3<br>+75.5°<br>(c=0.2, water) |

Note (1) measured in the form of free base.

Table 2

| Compound Number | Compound Name | Solvent System | Rf Value | Color reaction |
|---|---|---|---|---|
| 1 | fortimicin B | A | 0.56 | ninhydrin |
| 2 | fortimicin A | A | 0.47 | ninhydrin |
| 3 | fortimicin C | A | 0.43 | ninhydrin |
| 4 | 4-N-glycolylfortimicin B | A | 0.46 | iodine |
| 5 | 4-N-acetylfortimicin B | A | 0.43 | " |
| 6 | 4-N-propionylfortimicin B | A | 0.46 | " |
| 7 | 4-N-(n-butyryl)fortimicin B | A | 0.48 | " |
| 8 | 4-N-(n-valeryl)fortimicin B | A | 0.49 | " |
| 9 | 4-N-(β-alanyl)fortimicin B | A | 0.41 | " |
| 10 | 4-N-(γ-amino-n-butyryl)-fortimicin B | A | 0.44 | " |
| 11 | 4-N-(δ-amino-n-valeryl)-fortimicin B | A | 0.47 | " |
| 12 | 4-N-(ε-amino-n-caproyl)-fortimicin B | A | 0.42 | " |
| 13 | 4-N-glycylglycylfortimicin B | A | 0.42 | " |
| 14 | 4-N-[L-(-)-γ-amino-α-hydroxybutyryl]fortimicin B | A | 0.41 | " |
| 15 | 4-N-(2-aminoethyl)-fortimicin B | A | 0.41 | " |
| 16 | 4-N-ethylfortimicin B | A | 0.60 | " |

Table 2-continued

| Compound Number | Compound Name | Solvent System | Rf Value | Color reaction |
|---|---|---|---|---|
| 17 | 4-N-(n-propyl)fortimicin B | A | 0.66 | " |
| 18 | 4-N-(n-butyl)fortimicin B | A | 0.71 | " |
| 19 | 4-N-(n-pentyl)fortimicin B | A | 0.72 | " |
| 20 | 4-N-(3-aminopropyl)-fortimicin B | A | 0.43 | " |
| 21 | 4-N-(4-aminobutyl)-fortimicin B | A | 0.43 | " |
| 22 | 4-N-(5-aminopentyl)-fortimicin B | A | 0.47 | " |
| 23 | 4-N-(6-aminohexyl)-fortimicin B | A | 0.49 | " |
| 24 | 4-N-(2-hydroxyethyl)-fortimicin B | A | 0.46 | " |
| 25 | 4-N-[2-(2-aminoethyl)-aminoethyl]fortimicin B | A | 0.36 | " |
| 26 | 4-N-(2-methylaminoethyl)-fortimicin B | A | 0.43 | " |
| 27 | 4-N-[(S)-4-amino-2-hydroxybutyl]fortimicin B | A | 0.27 | " |
| 28 | 4-N-[(S)-4-methylamino-2-hydroxybutyl]fortimicin B | A | 0.34 | " |
| 29 | 4-N-[(R,S)-4-amino-2-hydroxy-butyl]fortimicin B | A | 0.27 | " |
| 30 | 4-N-[(R,S)-4-methylamino-2-hydroxybutyl]fortimicin B | A | 0.34 | " |
| 31 | 4-N-[(S)-3-amino-2-hydroxy-propyl]fortimicin B | A | 0.35 | " |
| 32 | 4-N-[(S)-3-methylamino-2-hydroxypropyl]fortimicin B | A | 0.40 | " |
| 33 | 4-N-[(S)-5-amino-2-hydroxy-pentyl]fortimicin B | A | 0.34 | " |
| 34 | 1,2',6'-tri-N-carbobenzoxy-fortimicin B | C | 0.47 | " |
| 35 | 1,2',6'-tri-N-t-butoxy-carbonylfortimicin B | C | 0.31 | " |
| 36 | tetra-N-carbobenzoxy-fortimicin A | B | 0.66 | " |
| 37 | tetra-N-carbobenzoxy-(4-N-glycylglycyl-fortimicin B) | B | 0.54 | " |
| 38 | tetra-N-carbobenzoxy-{4-N-[L-(-)-γ-amino-α-hydroxybutyl]fortimicin B} | B | 0.78 | " |
| 39 | 1,2',6'-tri-N-carbobenzoxy-4-N-ethylfortimicin B | C | 0.49 | " |
| 40 | tetra-N-carbobenzoxy-[4-N-(2-aminoethyl)fortimicin B] | C | 0.70 | " |
| 41 | tri-N-carbobenzoxy-[4-N-(2-methylaminoethyl)fortimicin B] | C | 0.15 | " |

Table 3-1

| Strain Name | Minimum inhibition concentration (MIC mcg/ml, pH 7.2) Compound Number | | | | | | | | |
|---|---|---|---|---|---|---|---|---|---|
| | 1 | 2 | 3 | 4 | 15 | 27 | 28 | 29 | KA* |
| *Staphylococcus aureus* 209-P | >100 | 0.78 | 3.12 | 3.12 | 0.78 | 0.4 | 0.78 | 0.4 | 0.4 |
| *Staphylococcus aureus* Smith (A) | 100 | 0.78 | 6.25 | 3.12 | 0.78 | 0.4 | 0.4 | 0.4 | 0.4 |
| *Staphylococcus a ureus* 226 | 100 | 0.78 | 6.25 | 12.5 | 0.4 | 0.4 | 0.4 | 0.78 | 0.78 |
| *Escherichia coli* NIHTC-2 | >100 | 3.12 | 12.5 | 12.5 | 3.12 | 3.12 | 1.56 | 3.12 | 1.56 |
| *Eschericihia coli* GN2411-5 | >100 | 6.25 | 25 | 12.5 | 3.12 | 6.25 | 6.25 | 6.25 | 3.12 |
| *Eschericihia coli* 3100 | 100 | 6.25 | 12.5 | 12.5 | 6.25 | 12.5 | 12.5 | 12.5 | 3.12 |
| *Klebsiella pneumoniae* KY4274 | 100 | 3.12 | 12.5 | 25 | 6.25 | 3.12 | 3.12 | 6.25 | >100 |
| *Proteus vulgaris* JJ | >100 | 3.12 | 12.5 | 25 | 6.25 | 3.12 | 3.12 | 3.12 | 1.56 |
| *Salmonella enteritidis* G-14 | 100 | 6.25 | 25 | 25 | 25 | 3.12 | 3.12 | 6.25 | 3.12 |
| *Shigella sonnei* ATCC9290 | >100 | 6.25 | 25 | 25 | 6.25 | 3.12 | 6.25 | 6.25 | 3.12 |
| *Pseudomonas aeruginosa* BMH#1 | >100 | 12.5 | 100 | 50 | 12.5 | 6.25 | 12.5 | 12.5 | 25 |
| *Escherichia coli* 76–2 1** | >100 | 3.12 | 12.5 | 6.25 | 3.12 | 3.12 | 3.12 | 3.12 | >100 |
| *Escherichia coli* 57R/W677 1** | >100 | 12.5 | 25 | 25 | 12.5 | 12.5 | 12.5 | 12.5 | >100 |
| *Escherichia coli* R12 Z-338 1** | >100 | 12.5 | 6.25 | 25 | 6.25 | 12.5 | 6.25 | 12.5 | 100 |
| *Escherichia coli* R18 KY8321 2** | >100 | 3.12 | 6.25 | 6.25 | 3.12 | 6.25 | 12.5 | 12.5 | >100 |
| *Escherichia coli* R17 Z343 3** | >100 | 1.56 | 3.12 | 6.25 | 0.78 | 3.12 | 3.12 | 3.12 | 12.5 |
| *Escherichia coli* R19 KY8348 4** | >100 | >100 | >100 | >100 | >100 | >100 | >100 | >100 | 1.56 |
| *Escherichia coli* R20 KY8349 5** | >100 | 3.12 | 12.5 | 12.5 | 3.12 | 1.25 | 1.25 | 3.12 | >100 |
| *Pseudomonas aeruginosa* UCLA 4184 | >100 | 25 | 50 | 100 | 12.5 | 25 | 50 | 25 | >100 |
| *Pseudomonas aeruginosa* R9 KY8516 3** | >100 | 50 | >100 | 100 | 25 | 25 | 50 | 50 | >100 |
| *Pseudomonas aeruginosa* R4 KY8511 4** | >100 | >100 | >100 | >100 | >100 | >100 | >100 | >100 | 100 |
| *Pseudomonas aeruginosa* R5 KY8512 6** | >100 | 12.5 | 50 | 50 | 12.5 | 6.25 | 12.5 | 12.5 | >100 |
| *Providencia sp* 164 7** | >100 | 25 | 100 | 100 | 12.5 | 25 | 25 | 25 | >100 |
| *Serratia marcescens* 1065 3** | >100 | 6.25 | 50 | 50 | 6.25 | 6.25 | 6.25 | 6.25 | 100 |
| *Klebsiella pneumoniae* 3020 Y-60 1** | >100 | 12.5 | 100 | >100 | 50 | 12.5 | 12.5 | 25 | >100 |

*KA: kanamycin A
**1: gentamicin, producing adenylsynthetase.
2: gentamicin, producing adenylsynthetase and neomycin phosphotransferase type II.
3: kanamycin, producing acetyltransferase.
4: gentamicin, producing acetyltransferase type I.
5: neomycin, producing phosphotransferase type I.
6: neomycin, producing phosphotransferase type I and type II.
7: gentamicin, producing acetyltransferase type II.
Bacteria inactivates the antibiotics by said enzyme.

Table 3-2

| Microorganism Compound Number | Minimum inhibition concentration (MIC mcg/ml pH 8.0) | | | | | | |
|---|---|---|---|---|---|---|---|
| | SA | BS | EC | PV | SS | ST | KP |
| 1 | 12.5 | 12.5 | 25 | 25 | 50 | 12.5 | 50 |
| 2 | 0.04 | 0.04 | 0.16 | 0.32 | 0.63 | 0.16 | 0.16 |
| 3 | 0.16 | 0.32 | 0.08 | 0.63 | 1.25 | 0.32 | 0.63 |
| 4 | 1.25 | 5 | 1.25 | 2.5 | 5 | 1.25 | 5 |
| 5 | 12.5 | 50 | 50 | 100 | 50 | 50 | >200 |
| 6 | 12.5 | 50 | 50 | 200 | >200 | 50 | >200 |
| 7 | 6.25 | 12.5 | 6.25 | 100 | 50 | 12.5 | 25 |
| 8 | 100 | 25 | >100 | >200 | >200 | >200 | >200 |
| 9 | 0.08 | 0.08 | 0.63 | 0.63 | 1.25 | 0.32 | 0.32 |
| 10 | 0.32 | 0.16 | 1.25 | 1.25 | 2.5 | 0.63 | 2.5 |
| 12 | >20 | >20 | >20 | >20 | >20 | >20 | >20 |

Table 3-2-continued

| | Minimum inhibition concentration (MIC mcg/ml pH 8.0) | | | | | | |
|---|---|---|---|---|---|---|---|
| Micro-organism Compound Number | SA | BS | EC | PV | SS | ST | KP |
| 13 | 0.32 | 0.32 | 1.25 | 2.5 | 5 | 1.25 | 2.5 |
| 14 | 0.63 | 5 | 0.63 | 10 | 20 | 2.5 | 5 |
| 15 | 0.16 | 0.16 | 0.32 | 0.64 | 1.25 | 0.32 | 0.63 |
| 16 | 1.56 | 3.13 | 3.13 | 6.25 | 6.25 | 3.13 | 50 |
| 17 | 3.13 | 12.5 | 6.25 | 12.5 | 12.5 | 6.25 | 100 |
| 18 | 12.5 | 25 | 25 | 100 | 25 | 12.5 | >200 |
| 19 | 25 | 200 | 100 | >200 | 100 | 100 | >200 |
| 20 | 1.25 | 2.5 | 5 | 10 | 20 | 1.25 | 80 |
| 21 | 0.32 | 0.32 | 1.25 | 2.5 | 2.5 | 1.25 | 5 |
| 22 | 1.25 | 0.63 | 5 | 10 | 5 | 2.5 | 20 |
| 23 | 5 | 5 | 20 | >80 | >80 | 20 | >80 |
| 24 | 1.25 | >80 | 5 | 10 | 10 | 1.25 | 40 |
| 25 | 0.63 | 1.25 | 1.25 | 5 | 5 | 1.25 | 5 |
| 26 | 0.04 | 0.32 | 0.16 | 1.25 | 5 | 1.25 | 5 |
| 27 | 0.04 | 0.04 | 0.16 | 0.32 | 1.25 | 0.16 | 0.32 |
| 28 | 0.04 | 0.04 | 0.08 | 0.32 | 0.63 | 0.08 | 0.32 |
| 29 | 0.08 | 0.04 | 0.16 | 0.32 | 0.63 | 0.16 | 0.63 |
| 30 | 0.08 | 0.02 | 0.32 | 0.16 | 0.63 | 0.08 | 0.32 |
| 31 | 0.16 | 0.32 | 2.5 | 1.25 | 2.5 | 0.63 | 2.5 |
| 32 | 0.16 | 0.63 | 2.5 | 2.5 | 2.5 | 0.63 | 5 |
| 33 | 0.32 | 1.25 | 2.5 | 5 | 1.25 | 10 | |

(Note): The compound of compound number 11 was unstable in an alkali condition (pH 8.0), and could not be measured its MIC values.

As is evident from the foregoing data, the compounds of the instant invention exhibit good antibacterial activity against various microorganisms and are, therefore, useful as antibacterial agents or antiseptics.

Similarly, the non-toxic acid addition salts of the instant compounds have a wide antibacterial spectrum and are useful as antibacterial agents, etc. As used herein, the term nontoxic acid addition salts means the mono-, di-, tri- and tetrasalts obtained by reaction of one molecule of the compound represented by said general formula (I) with 1 to 6 equivalents of pharmaceutically acceptable, non-toxic acids. Suitable acids include the inorganic acids such as sulfuric acid, hydrochloric acid, hydrobromic acid, hydriodic acid, phosphoric acid, carbonic acid, nitric acid, etc., and organic acids such as acetic acid, fumaric acid, malic acid, citric acid, mandelic acid, succinic acid, ascorbic acid, etc., amino acids such as aspartic acid, etc., and the like. Thus, the compositions of matter aspect of the present invention also include such pharmaceutically acceptable non-toxic acid addition salts.

The processes for synthesizing the compounds of the invention are generally illustrated in the following flow sheet I. As illustrated, the compounds are synthesized through (1) step 1, step 2 and step 3, (2) step 1, step 5 and step 7, or (3) step 1, step 2, step 6 and step 7.

More particularly, when the desired compound represented by the general formula (I) is a compound represented by $$R = -\underset{\underset{O}{\|}}{C} - R_1,$$

it is synthesized through step 1→step 2→step 3. When the desired compound represented by the general formula (I) is a compound represented by $R = -CH_2R_2$, it is synthesized through step 1→step 2→step 3→step 4 or through step 1→step 5→step 7, or through step 1→step 2→step 6→step 7.

Among the compounds represented by the general formula (I) thus obtained, the compounds represented by $R = CH_2R_2$ are more stable under a strongly alkaline conditions than the compounds represented by $R = COR_1$.

The individual steps of the foregoing process will be described in detail below. In the description, the compounds represented by the general formulae (I), (Ia), (Ib), (II) . . . (VII) are sometimes referred to as compounds (I), (Ia), (Ib), (II) . . . (VI), correspondingly.

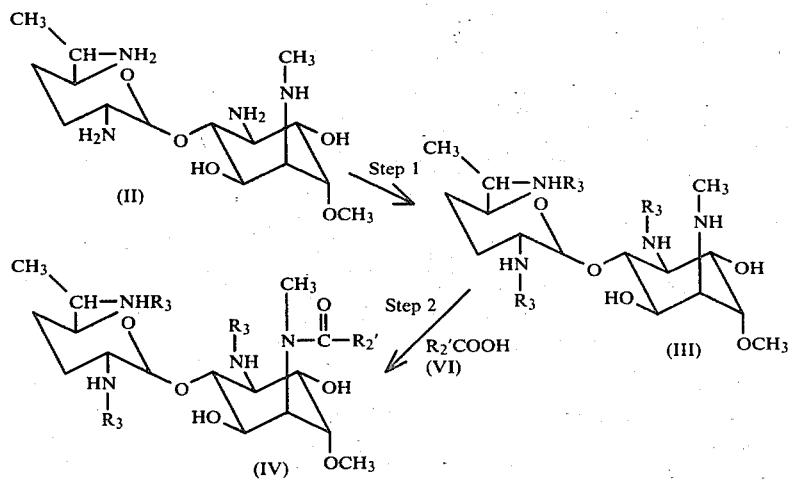

Flow Sheet 1

-continued
Flow Sheet 1

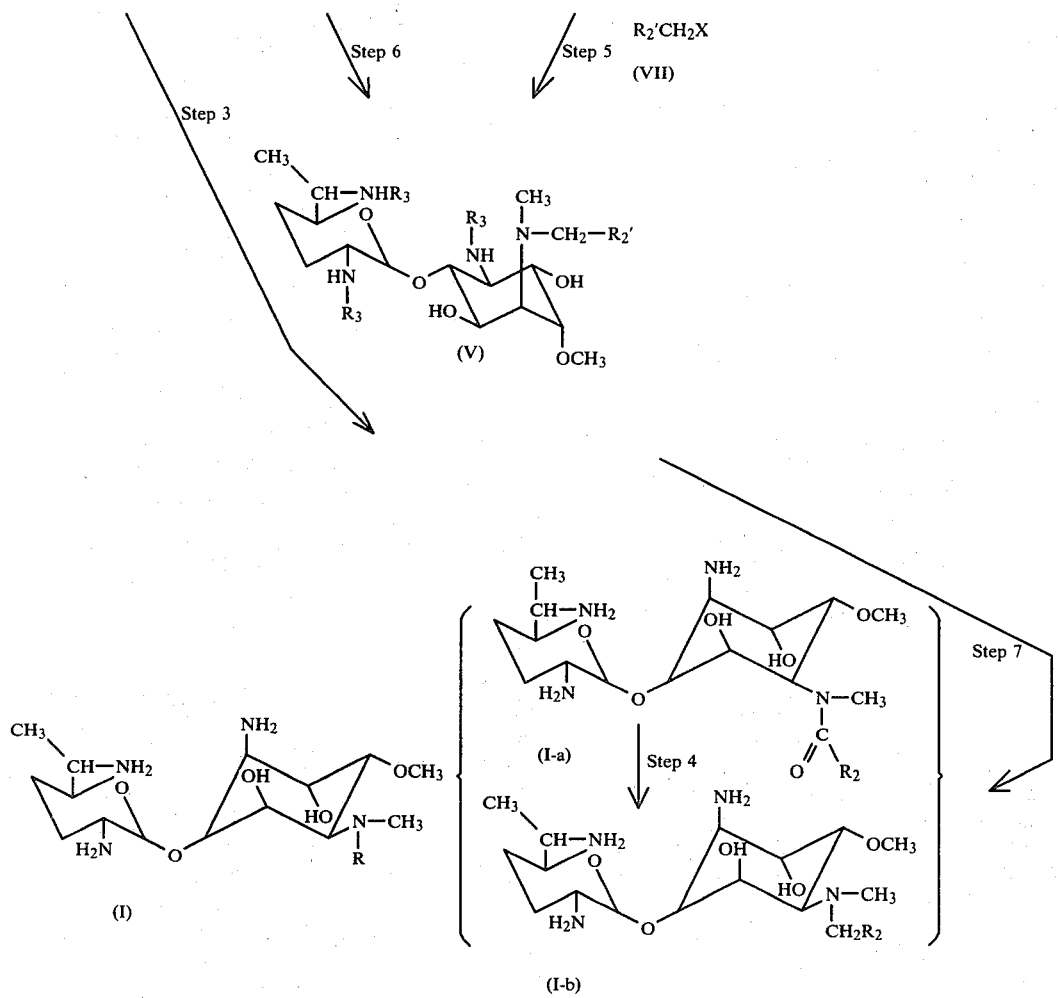

Step 1—Synthesis of compounds represented by formula (III) from fortimicin B A compound represented by formula (III) in which one of the hydrogen atoms of the amino group bonded to the carbon atoms at the 1-, 2'- and 6'-positions of fortimicin B is masked by an amino masking group ($R_3$), can be obtained by reacting fortimicin B free base with an amino-masking reagent in an appropriate solvent. For this step, amino-masking reagents usually employed in peptide synthesis can be utilized. Examples of suitable amino masking reagents are:

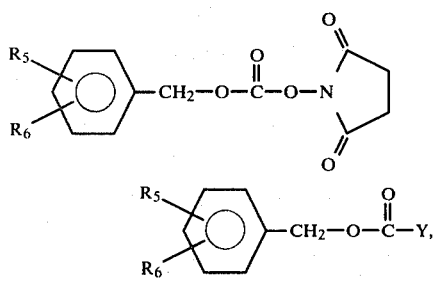

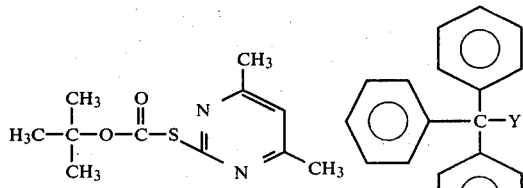

-continued

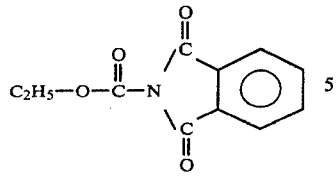

[wherein $R_5$ and $R_6$ may be same or different, and represent H, OH, $NO_2$, Cl, Br, I, alkyl groups (having 1 to 5 carbon atoms), alkoxy groups (having 1 to 5 carbon atoms); $R_7$ represents H, F, Cl, BR, I or an alkyl group (having 1 to 5 carbon atoms), and Y represents Cl, Br or I].

Suitable solvents for the reaction include dimethylformamide, dimethylacetamide, tetrahydrofuran, dioxane, 1,2-dimethoxyethane, methanol, ethanol, acetone, water, or mixtures thereof. Among these solvents, methanol is particularly preferable.

The concentration of fortimicin B in the reaction is appropriately 1 to 250 millimoles/l, and 10 to 100 millimoles/l is particularly preferred. The concentration of the amino-masking reagent is appropriately 4 millimoles/l to 1 mole/l, with 30 millimoles/l to 400 millimoles/l being preferable. The amount of the amino-masking reagent utilized in the reaction is appropriately 1 to 5 moles, and 3 to 4 moles per mole of fortimicin B is preferred. In that case it is not favorable when the amount of the amino-masking reagent is over 5 moles, because the hydrogen atom of the amino group bonded to the carbon atom at the 4-position of fortimicin B is also masked by the amino-masking group, and the yield of the desired formula (III) compound is lowered. On the other hand, it is not favorable, either, that the amount of the amino-masking reagent is below 1 mole, because the yield of the compound of formula (III) is lowered.

The reaction temperature is 0°–60° C., and preferably 0° C. to room temperature. Under such conditions the reaction time is usually 2 to 18 hours.

The compound represented by formula (III) synthesized according to the foregoing process can be utilized directly in the successive step as a reaction mixture or may be isolated and purified and then used in the next step.

Purification and isolation of the compound represented by formula (III) from the reaction mixture can be accomplished according to the following procedure. The solvent is distilled off from the reaction mixture, and a residue is obtained. The residue is triturated with an organic solvent such as chloroform or ethyl acetate to dissolve the extractable matters. Then, the resulting extract solution is subjected to column chromatography using silica gel (for example, Kieselgel 60 made by E. Merck, etc.). Elution is then carried out with an organic solvent such as chloroform-methanol, or ethyl acetate-ethanol, etc., and fractions showing a specific Rf value are collected and concentrated to dryness, whereby the desired material is obtained in the form of a white powder.

The compound represented by formula (III) thus obtained can be utilized as a raw material for preparing compounds represented by formulae (Ia) and (Ib) useful as antibacterial agents, etc.

The compound represented by formula (Ia) is unstable in alkali conditions and, therefore, it is desirable in the preparation of the compound represented by formula (III) to select an amino-masking reagent which does not require an alkaline condition to remove the masking group. Examples of amino-masking reagents satisfying these conditions are given below:

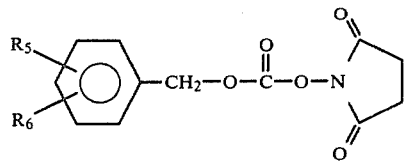

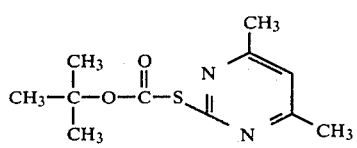

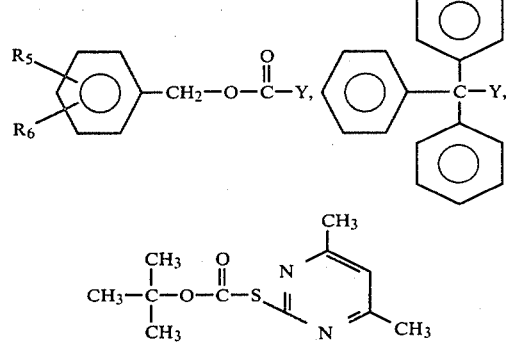

(wherein $R_5$, $R_6$ and Y have the same meanings as defined above).

The compound represented by formula (Ib) is stable in both acid and alkali conditions, and when the compound represented by formula (III) is utilized as a raw material for preparing the compound represented by formula (Ib), any amino-masking reagent can be utilized.

Step 2—Preparation of Compound (IV) from Compound (III)

Compound (IV) is obtained by acylating compound (III) with an ordinary acylating agent in an appropriate solvent.

The acylating agent used herein includes carboxylic acids represented by the general formula (VI), $R'_2COOH\{$wherein $R'_2$ represents an alkyl group, hydroxyalkyl group, carbamoylaminoalkyl group, N-alkylaminoalkyl group, N-alkylaminohydroxyalkyl group, substituted aminoalkyl group (the substituent represents an amino-masking group), substituted aminohydroxyalkyl group (the substituent represents an amino-masking group), N-substituted aminoalkyl group [the substituent represents a substituted aminomethylcarbonyl group (the substituent represents an amino-masking group)], where the amino-masking group may be same or different from said $R_3\}$, or derivatives of carboxylic acids functionally equivalent to these, i.e., acid anhydrides of the carboxylic acids represented by the general formula (VI), active esters of said carboxylic acids with a compound selected from the group consisting of

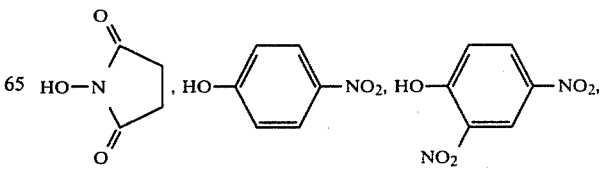

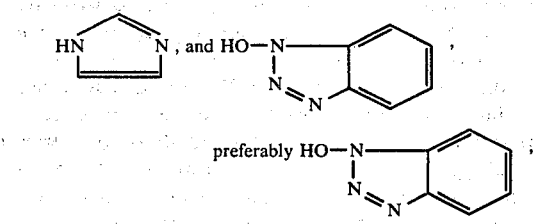

or acid halogenides, etc. of said carboxylic acids.

When the acylating agent used herein contains a free amino group, it is necessary to mask the amino group with an appropriate amino-masking group according to known procedures. Of course, it is preferable to utilize the same masking groups as the amino-masking groups at the 1-, 2'- and 6'-positions of the compound (III). The amino groups are masked in the same manner as in said step 1.

The concentration of the compound (III) used is in the range of from 1 to 250 mM, preferably 10 to 100 mM. Equal or more moles of the acylating agent is used to the compound (III). When an acid anhydride is used as the acylating agent, it is preferable to use 1 to 5 moles of the acid anhydride per mole of the compound (III). When an active ester is used as the acylating agent, it is preferable to use 1 to 1.5 moles of the active ester per mole of the compound (III).

Suitable solvents include dimethylformamide, dimethyl acetamide, tetrahydrofuran, dioxane, 1,2-dimethoxyethane, methanol, ethanol, water or mixtures thereof. Tetrahydrofuran is preferably used whatever acylating agent is used.

The reaction is carried out at a temperature of from 0° to 70° C., preferably 0° C. to room temperature, for 15 minutes to 20 hours and preferably 1 to 18 hours.

In addition to the foregoing procedure, a DCC method, or the like can be applied to the acylation step.

Thus, compound (IV) is formed in the reaction solution, and the reaction solution as such can be used in the preparation of compound (Ia), or the compound (IV) can be isolated and then used in the preparation of the compound (Ia).

Isolation and purification of the compound (IV) from the reaction solution is carried out by first distilling off the solvent from the reaction solution. The resulting residues are admixed with an organic solvent such as chloroform, ethyl acetate, etc. to extract the soluble portions. The extract is then subjected to column chromatography, using a column filled with silica gel such as Kieselgel 60 (trade name by E. Merck), or the like. Elution is carried out using an organic solvent system of chloroform-methanol, ethyl acetate-ethanol, etc., and fractions containing the compounds (IV) are collected. The solvent is then removed whereby the compound (IV) is obtained.

Step 3—Preparation of Compound (Ia) from Compound (IV)

The masking group $R_3$ of the amino group of the compound (IV) obtained by step 2 is removed according to known procedure to obtain compound (Ia). For example, when the masking group is a benzyloxycarbonyl group, the masking group can be removed by catalytic hydrogenolysis in the presence of a metal catalyst of palladiumcarbon, platinum, rhodium, etc., and in the presence of an acid such as hydrochloric acid, hydrobromic acid, acetic acid, etc. in a solvent of water, tetrahydrofuran, dimethylacetamide, dimethylformamide, lower alcohols, dioxane, ethyleneglycoldimethylether, or combinations thereof, etc., preferably in methanol at room temperature and atmospheric pressure, while passing hydrogen gas through the reaction mixture.

Usually 1 to 10% by weight of the metal catalyst is used on the basis of the compound (IV), and the concentration of compound (IV) is usually 1 to 200 mM, preferably about 50 mM.

The acid is added to the reaction mixture so that pH is maintained 4 or less. The end of the reaction can be confirmed by the completion of generation of carbon dioxide or by thin layer chromatography, and the like.

When the masking group is a tertiary butoxycarbonyl group, its removal can be carried out in the presence of hydrochloric acid or trifluoroacetic acid in a non-aqueous solvent, for example, dichloromethane, chloroform, trichloroethylene, and ethyl acetate. In such instance, compound (IV) is used at a concentration of 1 to 200 mM, preferably about 50 mM, and an equivalent amount or more of the acid is used. The completion of the reaction is confirmed by thin layer chromatography, etc.

When the masking group is a triphenylmethyl group the masking group can be removed by treatment with acetic acid or trifluoroacetic acid according to known procedure; and when the masking group is an orthonitrophenylsulfenyl group, the treatment is carried out with acetic acid or hydrochloric acid according to known procedure to remove the masking group.

Separation and purification of the desired product are carried out according to known procedure using an ion exchange resin, silica gel column chromatography or the like. For example, according to a procedure using ion exchange resin, the reaction mixture is filtered, if necessary, and the resulting filtrate is evaporated to dryness. The residues are dissolved in water and after the pH is adjusted to about 6 by an alkali, for example, sodium hydroxide, the resulting solution is passed through a column of, for example, Amberlite CG-50 (ammonium salt form) to adsorb the desired product. Then, the column is subjected to elution with an appropriate concentration of ammonia solution to divide the eluate into fractions. The fractions having an antibacterial activity are combined and evaporated to remove the solvent. The desired product is obtained as a powder.

Step 4—Preparation of Compound (Ib) from Compound (Ia)

The compound (Ia) obtained in step 3, or fortimicin A and fortimicin C obtained according to known methods is reduced in an appropriate solvent in the presence of a reducing agent for converting the carbonyl group in the amide group to a methylene group at room temperature or a solvent reflux temperature, whereby compound (Ib) is obtained.

As the solvent, tetrahydrofuran, dioxane, diethylether, etc. are appropriate. As the reducing agent, an excess amount, usually 10-fold or more of lithium aluminum hydride, diborane, etc. is used.

Purification of the desired product is carried out, for example, with ion exchange resin in the following manner. After the excess reducing agent in the reaction mixture is decomposed by ethyl acetate, water, or the like, most of the solvent is distilled off under reduced pressure. The resulting residues in a semi-solid state are admixed with water to extract watersoluble components, and the resulting extract is subjected to column chromatography in a column filled with weakly acidic ion exchange resin (for example, Amberlite CG-50). The column is washed with water, and then eluted with aqueous ammonia. Fractions containing the compound (Ib) are collected, and ammonia is removed by evaporation whereby the compound (Ib) is obtained as a white powder.

The separation and purification can be also carried out according to other known procedures, such as silica gel chromatography, etc.

Step 5—Preparation of Compound (IV) from Compound (III)

Compound (V) can be prepared by reacting compound (III) with a compound represented by the general formula (VII), $R_2'CH_2X$ (wherein $R_2'$ has the same meaning as defined above, and X represents chlorine, bromine, iodine, a methanesulfonylester group or p-toluenesulfonylester group) in an appropriate solvent to alkylate the compound (III). The concentration of the compound (III) used in the reaction is in a range of 1 to 250 mM/l, preferably 10 to 100 mM/l. The amount of the compound (VII) used is 0.5 to 2 moles, preferably 0.8 to 1.2 moles per mole of compound (III).

Suitable solvents include methanol, ethanol, propanol, butanol, tetrahydrofuran, acetone or their mixtures, and ethanol is preferably used.

The reaction is carried out at a temperature range of 0° to 120° C., preferably 10° to 80° C., for 2 to 24 hours, preferably 10 to 20 hours. The desired product thus obtained can be used, as such, in the next reaction without isolation or maybe first isolated and purified in the following manner.

After the completion of the reaction, the solvent is distilled off from the reaction mixture, and the residue is dissolved in an organic solvent such as ethyl acetate, chloroform, etc. After the organic solution is washed with water and dried, the solvent is evaporated. Then, the residue is applied to silica gel column chromatography in a column filled with silica gel using, for example, (Kieselgel 60, trade name of E. Merck Co.). Elution is then carried out with an organic solvent such as chloroform-methanol, ethyl acetate-ethanol, etc., and fractions containing compound (V), checked by Rf values, are collected. The solvent is removed by distillation, whereby compound (V) is obtained as a white powder.

Step 6—Preparation of Compound (V) from Compound (IV)

Compound (V) can be obtained by reducing compound (IV) obtained in step 2 in the presence of a reducing agent for converting the carbonyl group in the amide group to a methylene group in an appropriate non-aqueous solvent at room temperature or a solvent reflux temperature.

For this step, suitable solvents include tetrahydrofuran, dioxane, diethylether, etc. and combinations thereof. As the reducing agent, diborane, lithium aluminum hydride, etc. are used. In this reaction, compound (IV) is used at a concentration of 1 to 250 mM, preferably 10 to 100 mM, and usually 10-fold or more equivalents of the reducing agent is used. The reaction is usually completed in from 10 minutes to 18 hours.

When the amino group of compound (IV) used in this step is masked by a benzyloxycarbonyl group, it is preferable to use diborane as the reducing agent because the carbonyl group in the amide group is converted to the methylene group without impairing the benzyloxycarbonyl group of the compound (IV). Consequently compound (V) can be obtained in good yield. [W. V. Curran and R. B. Angier: J. Org. Chem., 31, 3867 (1966)].

When $R_2'$ of compound (IV) used has a masked amino group in this step 6, similar compounds, in addition to compound (V), are formed, depending upon the masking group, reaction conditions, and reducing agent. That is, when diborane is used as the reducing agent, and the masking group at the masked amino group of $R_2'$ of compound (IV) is a benzyloxycarbonyl group or a t-butyloxycarbonyl group, compound (V), and compounds in which the masking group at the amino group of $R_2'$ of the compound (V) is reduced to a methyl group, are obtained. If the reaction time is shorter, the former is principally formed and if the reaction time is prolonged, the yield of the latter is increased.

The resulting reaction product can be used as a raw material for step 7, as such, without isolating compound (V). Alternatively compound (V) can be isolated in the following manner. The solvent is distilled off from the reaction mixture, and then the residue is admixed with water to decompose the remaining hydride. Then, an organic solvent such as ethyl acetate, chloroform, etc. is added thereto to extract the soluble components. After separation of the aqueous layer, the organic solvent layer is washed with water, dried with anhydrous sodium sulfate, etc., and the solvent is distilled off. The residue is dissolved in an organic solvent such as chloroform, etc., and the desired product is obtained by silica gel column chromatography.

When two end products are involved, these two products can be separately obtained by fractionating the eluates, and if necessary by changing the eluting solvent.

Step 7—Preparation of Compound (Ib) from Compound (V)

According to this step, the amino-masking group, $R_3$, of 1, 2', 6'-tri-N-masked-4-N-alkyl (or substituted alkyl) fortimicin B [compound (V)] obtained in said step 5 or 6 is removed according to the known procedure based on step 3 in which the compound (V) is used in place of the compound (IV), whereby 4-N-alkyl (or substituted alkyl)fortimicin B [compound (Ib)] is obtained.

An acid addition salt of compound (I) thus prepared can be obtained according to the following procedure. The compound is first dissolved in water, and then admixed with an acid. Then, a solvent capable of lowering the solubility of the salt of compound (I), for example, ethanol, etc. is added to form a precipitate. The precipitate is filtered and dried, whereby a white or grey powder of the acid addition salts of compound (I) is obtained.

Certain specific embodiments of the invention are illustrated by the following representation examples wherein Examples 1–2 illustrate embodiments for carrying out step 1, Examples 3–10 and 27 illustrate embodiments for carrying out step 2, Examples 11–18 illustrate embodiments for carrying out step 3, Examples 19–21 illustrate embodiments for carrying out step 4, Example 22 illustrates embodiments for carrying out step 5, Examples 23 and 28 illustrate embodiments for carrying out step 6, and Examples 24, 25, 26, and 29 illustrate embodiments for carrying out step 7.

EXAMPLE 1

Preparation of 1,2',6'-tri-N-benzyloxycarbonyl fortimicin B

In this example, 1.8 g (5.2 millimoles) of fortimicin B and 3 ml of triethylamine were dissolved in 100 ml of methanol, and a solution of 4.0 g (16.0 millimoles) of N-(benzyloxycarbonyloxy)succinimide in 50 ml of tetrahydrofuran was added dropwise thereto with stirring under ice cooling (3°–5° C.) over a period of 1.5 hours. After the completion of this addition, the solution was stirred for 2 hours under ice cooling (3°–5° C.), and then the solvent was evaporated under a reduced pressure. The residue (solid matter) thus obtained was dissolved in 200 ml of chloroform, and the resulting solution was washed successively with 100 ml each of an aqueous 5% sodium bicarbonate solution and water. After the washing, the chloroform solution was dried over anhydrous sodium sulfate, and concentrated to dryness under reduced pressure. The resulting solid residue was then dissolved in a small amount of chloroform, and the chloroform solution was charged into a column packed with 200 g of silica gel [Kieselgel 60, tradename, E. Merck Co.]. In this step, elution was carried out with a mixed solvent of methanol and chloroform (3:97 by volume) and an elute was taken in 60 ml fractions. Fractions Nos. 23–50 containing compounds having an Rf value 0.47 in solvent system C in Table 2 were combined. These fractions were concentrated to dryness under reduced pressure. As a result 2.3 g of white powder was obtained.

Melting point: 79°–82° C.

PMR spectrum (methanol-d$_4$): δ(ppm) 1.02 (3H,d), 1.2–1.6 (4H,m), 2.30 (3H,s), 2.90 (1H,t), 3.42 (3H,s), 3.5–4.0 (8H,m), 5.02 (6H,s), 5.36 (1H,d), 7.24 (15H,s). $[\alpha]_D^{23°} = +20.3°$ (c=1.0, methanol).

Elemental analysis as $C_{39}H_{50}N_4O_{11}$: Found: C 62.68, H 6.93, N 7.17 (%); Calculated: C 62.38, H 6.71, N 7.46 (%).

From the data above described, it was confirmed that the obtained product was 1,2',6'-tri-N-benzyloxycarbonyl fortimicin B, (3.1 millimoles, yield 59.6%).

EXAMPLE 2

Preparation of 1,2',6'-tri-N-t-butoxycarbonylfortimicin B

In this example 348 mg (1.0 millimoles) of fortimicin B was dissolved in 15 ml of methanol, and admixed with 960 mg (4.0 millimoles) of t-butyl-S-4,6-dimethylpyrimidin-2-ylthiocarbonate synthesized according to a manner similar to that described in Bull. Chem. Soc., Japan, 46, 1269, (1973) by T. Nagasawa et al. The reaction mixture was allowed to stand at room temperature for 5 days with moderate stirring. The reaction mixture thus obtained was then concentrated to dryness under reduced pressure. Thereafter, 30 ml of ethylacetate and 20 ml of water were added to the residue and the mixture was stirred. The ethylacetated layer was washed twice with 20 ml of water and then dried over anhydrous sodium sulfate. After drying, ethylacetate was evaporated under reduced pressure to obtain a solid residue. The resulting solid residue was dissolved in a small amount of chloroform and the chloroform solution was charged into a column packed with 20 g of silica gel.

In this step, elution was carried out with a mixed solvent of methanol and chloroform (3:97 by volume) and the eluate was taken in 6 ml fractions. Fractions Nos. 20–60 containing compounds having an Rf=0.31 in solvent system C in Table 2 were combined. These fractions were concentrated to dryness under reduced pressure. As a result 175 mg of a white powder was obtained.

PMR spectrum (methanol-d$_4$): δ(ppm) 1.10 (3H,d), 1.2–1.6 (4H,m), 1.59 (27H,s), 2.35 (3H,s), 3.5–4.0 (8H,m), 5.33 (1H,d).

Elemental analysis as $C_{30}H_{56}N_4O_{11}$: Found: C 55.24, H 8.70, N 8.59; Calculated: C 55.54, H 8.70, N 8.64.

From the data above described, it was confirmed that the product was 1,2,6'-tri-N-t-butoxycarbonylfortimicin B. (0.27 millimoles, yield 27%)

EXAMPLE 3

In this example 1 ml of N,N-dimethylformamide, 33 mg (0.28 millimole) of hydantoic acid and 38 mg (0.28 millimole) of 1-hydroxybenzotriazole were dissolved. 58 mg (0.28 millimole) of N,N'-dicyclohexycarbodiimide was added thereto, and the reaction mixture was stirred under ice cooling (3°–5° C.) for two hours.

The resulting solution was admixed with 164 mg (0.25 millimole) of 1,2,6'-tri-N-t-butoxycarbonylfortimicin B obtained in Example 2 and allowed to stand at room temperature for 2 days with stirring. Then, deposited insolubles were removed by filtration, and the filtrate was concentrated under reduced pressure to obtain a yellowish white solid residue [1,2',6'-tri-N-t-butoxycarbonyl-4-N-hydantoylfortimicin B].

EXAMPLE 4

In this example, 751 mg (1.0 millimole) of 1,2', 6'-tri-N-benzyloxycarbonylfortimicin B obtained in a similar method as in Example 1 was dissolved in 20 ml of methanol and 0.5 ml (5.0 millimoles) of acetic anhydride was added thereto. The resulting reaction mixture was allowed to stand at room temperature for 16 hours. The resulting solution was then concentrated under reduced pressure and the residue was dissolved in 20 ml of ethyl acetate and the solution was then washed successively with 10 ml each of an aqueous 5% sodium bicarbonate solution and water and then dehydrated with anhydrous sodium sulfate. After drying, the ethyl acetate solution was evaporated under reduced pressure and 10 ml of n-hexane was added to the residue to wash the residue with stirring. The n-hexane was removed by decantation to obtain a light yellowish white solid residue (1,2',6'-tri-N-benzyloxycarbonly-4-N-acetylfortimicin B).

EXAMPLE 5

In this example the reactions were carried out using the method of Example 4 using an acid anhydride shown in Table A to obtain a residue containing the compound (IV) shown in Table A. However, equal molar amounts of the acid anhydride shown in Table A were used in place of the acetic anhydride used in Example 4.

Table A

| Compound used in place of acetic anhydride | Compound (IV) |
| --- | --- |
| Propionic anhydride | 1,2',6'-tri-N-benzyloxycarbonyl-4-N-propionylfortimicin B |
| n-butyric anhydride | 1,2',6'-tri-N-benzyloxycarbonyl-4-N-(n-butyryl)fortimicin B |
| n-valeric anhydride | 1,2',6'-tri-N-benzyloxycarbonyl-4-N-(n-valeryl)fortimicin B |

EXAMPLE 6

In this example 10 ml of tetrahydrofuran, 230 mg (1.1 millimoles) of N-benzyloxycarbonylglycine, 148 mg (1.1 millimoles) of 1-hydroxybenzotriazole and 227 mg (1.1 millimoles) of N,N'-dicyclohexylcarbodiimide were dissolved and the resulting reaction mixture was stirred under ice cooling (3°–5° C.) for one hour. Then, 750 mg (1.0 millimole) of 1,2',6'-tri-N-benzyloxycarbonylfortimicin B obtained in a similar manner as in Example 1 was added thereto. The resulting mixture was stirred at room temperature for 18 hours. Then, insolubles were removed by filtration and the solvent in the filtrate was removed under reduced pressure. The resulting concentrate, dissolved in a small portion (2 ml) of chloroform, was charged into a column packed with 50 g of a silica gel. Elution was carried out with a mixed solvent of chloroform: methanol (98:2 by volume), and the eluate was taken in 6 ml fractions.

Fractions Nos. 24-40 were combined in which fractions are contained compounds having an Rf value 0.66 in solvent system B in Table 2. These fractions were concentrated to dryness under reduced pressure. As a result 612 mg of a white powder was obtained having the following PMR spectrum data (methanol-$d_4$): $\delta$(ppm), 1.12 (3H,d), 1.2–1.9 (4H,m), 2.98 and 3.06 (3H jointly, s, each), 3.33 (3H,s), 3.2–4.5 (11H,br), 4.95 (1H,d), 5.02 (8H,s), 7.20 (20H,s). It was thus confirmed that the product was tetra-N-benzyloxycarbonylfortimicin A. (0.67 millimole, yield 67%).

EXAMPLE 7

In this example, the same reactions were carried out in a similar manner as in Example 6 using the N-benzyloxycarbonyl derivatives shown in Table B to obtain the compounds (IV) shown in Table B, in which reaction equal molar amounts of N-benzyloxycarbonyl derivatives shown in Table B were used in place of N-benzyloxycarbonylglycine used in Example 6.

Table B

| Compound used in place of N-benzyloxycarbonyl-glycine | Compound (IV) |
| --- | --- |
| N-benzyloxycarbonyl-$\beta$-alanine | tetra-N-benzyloxycarbonyl-[4-N-($\beta$-alanylfortimicin B)] |
| N-benzyloxycarbonyl-$\gamma$-amino-n-butyric acid | tetra-N-benzyloxycarbonyl-[4-N-($\gamma$-amino-n-butyrylfortimicin B)] |
| N-benzyloxycarbonyl-$\delta$-amino-n-valeric acid | tetra-N-benzyloxycarbonyl-[4-N-($\delta$-amino-valerylfortimicin B)] |
| N-benzyloxycarbonyl-$\epsilon$-amino-n-caproic acid | tetra-N-benzyloxycarbonyl-[4-N-($\epsilon$-amino-n-caproylfortimicin B)] |

EXAMPLE 8

In this example 5 ml of tetrahydrofuran, 183 mg (1.1 millimoles) of O-benzylglycolic acid and 148 mg (1.1 millimoles) of 1-hydroxybenzotriazole were dissolved and the resulting reaction mixture was stirred under ice cooling (3°–5° C.). Then, 227 mg (1.1 millimoles) of N,N'-dicyclohexylcarbodiimide was added thereto, and after stirring under ice cooling (3°–5° C.) for three hours, 751 mg (1.0 millimole) of 1,2',6'-tri-N-benzyloxycarbonyl fortimicin B obtained in a similar manner as in Example 1 was added thereto. The resulting mixture was then stirred at room temperature for 17 hours. Deposited insolubles were removed by filtration and the solvent in the filtrate was removed under reduced pressure. As a result, a light yellowish white solid residue [1,2',6'-tri-N-benzyloxycarbonyl-4-N-(O-benzylglycolyl) fortimicin B] was obtained.

EXAMPLE 9

In this example 30 ml of tetrahydrofuran, 546 mg (2.1 millimoles) of N-benzyloxycarbonylglycylglycine and 279 mg (2.1 millimoles) of 1-hydroxybenzotriazole were dissolved and the resulting reaction mixture was stirred under ice cooling (3°–5° C.). Then, 426 mg (2.1 millimoles) of N,N'-dicyclohexylcarbodiimide was added thereto, and after stirring under ice cooling (3°–5° C.) for 2 hours, 1.50 g. (2.0 millimoles) of 1,2',6'-tri-N-benzyloxycarbonylfortimicin B obtained in a similar manner as in Example 1 was added thereto. The resulting reaction mixture was stirred at room temperature for 18 hours. Deposited insolubles were removed by filtration and the solvent in the filtrate was removed under reduced pressure. The resulting concentrate, dissolved in a small portion (2 ml) of chloroform, was charged into a column packed with 100 g of a silica gel. In this step, 450 ml of a mixed solvent of methanol and chloroform (2:98 by volume) was used for washing the column and elution was also carried out with the same solvent. The eluate was taken in 17 ml fractions. Fractions Nos. 18–60 were combined in which fractions are contained the compounds having an Rf value of 0.54 in solvent system B in Table 2. These fractions were concentrated to obtain 1.25 g of a white powder.

From elemental analysis as $C_{51}H_{62}N_6O_{15}$, that is, Found: C 61.02, H 6.15, N 8.41 (%); Calculated: C 61.31, H 6.26, N 8.41 (%).

it was confirmed that the obtained product was tetra-N-benzyloxycarbonyl-(4-N-glycylglycylfortimicin B) (1.3 millimoles, yield 60%).

EXAMPLE 10

In this example 20 ml of tetrahydrofuran, 557 mg (2.2 millimoles) of L-(−)-$\gamma$-benzyloxycarbonylamino-$\alpha$-hydroxybutyric acid and 297 mg (2.2 millimoles) of 1-hydroxybenzotriazole were dissolved and the resulting reaction mixture was stirred under ice cooling (3°–5° C.) Then, 454 mg (2.2 millimoles) of N,N'-dicyclohexylcarbodiimide was addded thereto, and after stirring under ice cooling (3°–5° C.) for 1 hour, 1.52 g (2.0 millimoles) of 1,2',6'-tri-N-benzyloxycarbonylfortimicin B obtained in a similar manner as in Example 1 was added thereto. The resulting reaction mixture was stirred at room temperature for 16 hours. Deposited insolubles were removed by filtration and the solvent in the filtrate was removed under reduced pressure. The resulting concentrate, dissolved in a small portion (2 ml) of chloroform, was charged into a column packed with 100 g of a silica gel. In this step, 350 ml of a mixed solvent of methanol and chloroform (2:98 by volume) was used for washing the column and elution was also carried out with the same solvent. The eluate was taken in 15 ml fractions. Fraction Nos. 15–45 were combined in which fractions are contained the compounds having an Rf value of 0.78 in solvent system B in Table 2. These fractions were concentrated to obtain 792 mg of a white powder having the following PMR data (methanol-$d_4$), $\delta$(ppm), 1.12 (3H,d), 1.2–2.0 (4H,br), 3.03 (3H,s), 3.33 (3H,s), 5.05 (8H,s), 7.26 (20H,s), It was thus confirmed that the product was tetra-N-benzyloxycarbonyl-{4-N-[L-(−)-$\gamma$-amino-$\alpha$-hydroxybutyryl]fortimicin B} (0.8 millimole, yield 40%).

EXAMPLE 11

In this example, the solid residues (1,2',6'-tri-N-t-butoxycarbonyl-4-N-hydantoylfortimicin B) obtained in Example 3 were dissolved in 10 ml of a mixed solvent of trifluoroacetic and dichloromethane (1:1 by volume), and the resulting reaction mixture was allowed to stand with stirring at room temperature for 16 hours. The solvent was removed under reduced pressure. Then 5 ml of water was added to the resulting concentrate and insolubles were removed by filtration. The filtrate, adjusted to pH 6 by using 1 N sodium hydroxide, was charged into a column packed with 10 ml of Amberlite CG-50 ($NH_4^+$ form, tradename, Rohm and Haas Company). After charging, 50 ml of water was used for washing the column, and then elution was carried out with 0.15 N aqueous ammonia. The eluate was taken in 2 ml fractions. Fraction Nos. 31–45 were combined in which fractions are contained the compounds having an Rf value of 0.43 in solvent system A in Table 2. These fractions were concentrated to obtain 67 mg of a white powder.

The melting point, PMR spectrum, mass spectrum, $[\alpha]_D$ and Rf value of thin layer chromatography of the thus obtained compound were completely identical with those of fortimicin C. Thus, it was identified that the compound was 4-N-hydantoylfortimicin B (fortimicin C). Yield 60%.

EXAMPLE 12

In this example concentrated hydrochloric acid (12 N) is diluted (60 times) with methanol to make a 0.2 N hydrochloric acid-methanol solution. Hydrochloric acid-methanol solutions having various normality hereinafter used are prepared by a similar manner.

In 20 ml of 0.2 N hydrochloric acid-methanol solution, a solid residue [1,2',6'-tri-N-benzyloxycarbonyl-4-N-acetylfortimicin B] obtained in Example 5 was dissolved and 40 mg of 10% palladiumcharcoal was added thereto. Then, hydrogen gas was bubbled through the reaction mixture at room temperature under atmospheric pressure for 16 hours. After the completion of the hydrogenation reaction, the catalyst was removed by filtration and the solvent in the filtrate was removed under reduced pressure. The resulting concentrate, dissolved in 5 ml of water, was charged into a column packed with 20 ml of Amberlite CG-50 ($NH_4^+$ form) after adjusting the resulting solution to pH 6 using 1 N sodium hydroxide. After charging, the column was washed with 60 ml of water, and then elution was carried out with 0.15 N aqueous ammonia. The eluate was taken in 5 ml fractions. Fractions Nos. 16–31 were combined in which fractions are contained the compound having an Rf value of 0.43 in solvent system A in Table 2. These fractions were concentrated to obtain 300 mg of a white powder having the following physical properties.

Mass spectrum m/e 391 ($M^+ +1$), 390 ($M^+$), 373, 355, 347, 310, 299, 277, 259, 249, 231, 181, 143, 97, 43.

PMR spectrum (deuterium oxide) $\delta$(ppm): 1.04 (3H,d), 1.2–1.9 (4H,m), 2.18 (3H,s), 2.8 (3H,br), 3.12 (3H,s), 3.44 (3H,s), 3.5 (2H,br), 3.86 (1H,q), 4.08 (1H,q), 4.16 (1H,t), 4.36 (1H,t), 4.80 (1H,d), 4.90 (1H,q).

From the above data, the compound was identified as 4-N-acetylfortimicin B. Yield 77%. Then 250 mg (0.64 millimole) of 4-N-acetylfortimicin B obtained above described was dissolved in 2 ml of water and the solution was adjusted to pH 2 with 5 N sulfuric acid. The thus obtained solution was poured into 20 ml of ethanol to precipitate at room temperature. After filtration and drying, 352 mg (0.57 millimole) of 4-N-acetylfortimicin B sulfate was obtained. Yield 85%. $[\alpha]_D^{25°} = +139.2°$ (c=1.0, water).

EXAMPLE 13

In this example, similar reactions, isolations and purifications were repeated as in Example 12, except that residues containing 1,2',6'-tri-N-benzyloxycarbonyl-4-N-propionylfortimicin B, 1,2',6'-tri-N-benzyloxycarbonyl-4-N-(n-valeryl) fortimicin B, obtained in Example 5, were used, respectively, in place of the starting material, that is, the residues [1,2',6'-tri-N-benzyloxycarbonyl-4-N-acetylfortimicin B] used in Example 12. As a result, 266 mg, 314 mg and 260 mg of white powder were obtained (each free base). The physical properties of the thus obtained compounds are shown below.

Product obtained when using 1,2',6'-tri-N-benzyloxycarbonyl-4-N-propionylfortimicin B as the starting material:

Mass spectrum m/e 405 ($M^+ +1$), 404 ($M^+$), 387, 369, 361, 331, 324, 299, 291, 273, 263, 245, 227, 212, 195, 143, 126, 97.

PMR (deuterium oxide): $\delta$(ppm) 1.02 (3H,d), 1.08 (3H,t) 1.2–1.9 (4H,m), 2.46 (2H,q), 2.8 (2H,br), 3.13 (3H,s), 3.45 (3H,s), 3.5 (2H,br), 3.87 (1H,q), 4.10 (1H,q), 4.17 1H,t), 4.33 (1H,t), 4.79 (1H,d), 4.91 (1H,q).

Sulfate $[\alpha]_D^{25°} = +136.8°$ (c=1.0, water).

From these physical properties, the compound was identified as 4-N-propionylfortimicin B. (0.66 millimole, yield 66%)

Product obtained when using 1,2',6'-tri-N-benzyloxycarbonyl-4-N-(n-butyryl)fortimicin B as a starting material:

Mass spectrum m/e 419 ($M^+ +1$), 418 ($M^+$), 338, 305, 299, 287, 277, 259, 241, 226, 209, 143, 126, 97, 43, PMR (deuterium oxide): $\delta$(ppm) 0.98 (3H,t), 1.00 (3H,d), 1.2–1.9 (6H,br), 2.42 (2H,q), 218 (2H,br), 3.02 and 3.14 (3H,s), 3.42 (3H,s), 3.5 (2H,br), 3.85 (1H,q), 4.10 (1H,q), 4.16 (1H,m), 4.35 (1H,t), 4.80 (1H,d), 4.89 (1H,q).

Sulfate $[\alpha]_D^{25°} = +131.0°$ (c=1.0, water).

From these physical properties, the compound was identified as 4-N-(n-butyryl)fortimicin B. (0.75 millimole, yield 75%).

Product obtained when using 1,2',6'-tri-N-benzyloxycarbonyl-4-N-(n-valeryl)fortimicin B as a starting material:

Mass spectrum m/e 433 ($M^+ +1$), 432 ($M^+$), 415, 319, 301, 299, 291, 273, 233, 171, 143, 97, 43.

PMR (deuterium oxide): $\delta$(ppm) 0.96 (3H,t), 1.02 (3H,d), 1.1–1.9 (8H,br), 2.40 (2H,br), 2.90 (2H,br), 3.00 and 3.18 (3H,s), 3.43 (3H,s), 3.45 (2H,br), 3.90 (1H,q), 4.18 (1H,m), 4.33 (1H,m), 4.82 (1H,d), 4.90 (1H,q).

Sulfate $[\alpha]_D^{25°} = 116.3°$ (c=1.0, water).

From these physical properties, the compound was identified as 4-N-(n-valeryl)fortimicin B (0.60 millimole, yield 60%).

EXAMPLE 14

In this example 20 ml of 0.2 N-hydrochloric acid-methanol solution, 500 mg (0.53 millimole) of tetra-N-benzyloxycarbonylfortimicin A obtained in Example 6 was dissolved and about 30 mg of 10% palladium-charcoal was added thereto. Then, hydrogen gas was bubbled through the reaction mixture at room temperature under atmospheric pressure for 18 hours. After the completion of the hydrogenation reaction, the catalyst was removed by filtration, and the solvent in the filtrate was removed under reduced pressure. The resulting concentrate, dissolved in 5 ml of water, was charged into a column packed with 5 ml of Dowex×4 (OH⁻ form, product of Dow Chemical Co., Ltd., U.S.A.). After charging, 15 ml of water was used for washing the column.

Combined eluates were concentrated to obtain 212 mg (0.50 millimole) of white powder. This powder was completely identical with fortimicin A standard in melting point, PMR spectrum, mass spectrum, $[\alpha]_D$ and Rf value of thin layer chloromatography.

In 2 ml of water, 170 mg (1.40 millimoles) of fortimicin A thus obtained was dissolved and adjusted to pH 2 with 5 N sulfuric acid. The resulting solution was added dropwise to 20 ml of ethanol and after filtration of the resulting precipitate 225 mg (0.33 millimole) of fortimicin A sulfate was obtained. (Yield 83%)

Sulfate $[\alpha]_D = +85.9°$ (c=1.0, water).

EXAMPLE 15

In this example, similar ractions, isolations and purifications as in Example 14 were used, except that 0.50 millimole each of tetra-N-benzyloxycarbonyl-[4-N-(β-alanyl)-fortimicin B], tetra-N-benzyloxycarbonyl-[4-N-(γ-amino-n-butyryl)-fortimicin B], tetra-N-benzyloxycarbonyl-[4-N-(δ-amino-n-valeryl) fortimicin B] and tetra-N-benzyloxycarbonyl-[4-N-(ε-amino-n-caproyl)-fortimicin B], obtained in Example 7, were used, respectively, in place of the starting material. As a result, 235 mg (free base), 298 mg (free base), 310 mg (hydrochloride) (only this compound was isolated as a hydrochloride, since decomposition took place through the step of preparing the sulfate according to a similar manner disclosed in Example 14) and 308 mg (free base) were obtained respectively. Physical properties of the respective products are shown below.

Product obtained when using tetra-N-benzyloxycarbonyl-[4-N-(β-alanyl)fortimicin B] as a starting material:

Mass spectrum m/e 419 (M⁺), 402, 306, 288, 278, 271, 260, 235, 231, 214, 207, 143, 126, 97186.

Sulfate $[\alpha]^{23°}_D = +80.6°$ (c=1.0, water).

Elemental analysis as $C_{18}H_{37}N_5O_6.2H_2SO_4.C_2H_5OH.2.5H_2O$: Found: C 32.96, H 7.41, N 9.71; Calculated: C 33.14, H 7.51, N 9.66.

From these physical properties, the compound was identified as 4-N-(β-alanyl)fortimicin B. (Yield 96%)

Product obtained when using tetra-N-benzyloxycarbonyl-[4-N-(γ-amino-n-butyryl)fortimicin B] as a starting material:

Mass spectrum m/e 434 (M⁺+1), 433 (M⁺), 415, 390, 349, 331, 320, 302, 274, 235, 217, 207, 202, 189, 143, 126, 97, 86.

Sulfate $[\alpha]^{23°}_D = +81.8°$ (c=1.0, water).

Elemental analysis as $C_{19}H_{39}N_5O_6.2H_2SO_4.C_2H_5OH.4H_2O$: Found: C 33.66, H 7.44, N 9.30. Calculated: C 33.73, H 7.68, N 9.36.

From these physical properties, the compound was identified as 4-N-(γ-amino-n-butyryl)fortimicin B. Yield 93%.

Product obtained when using tetra-N-benzyloxycarbonyl [4-N-(δ-amino-n-valeryl)fortimicin B] as a starting material:

Hydrochloride $[\alpha]^{23°}_D = +89.5°$ (c=1.0, water).

It was presumed that the compound was 4-N-(δ-amino-n-valeryl)fortimicin B.

Product obtained when using tetra-N-benzyloxycarbonyl [4-N-(ε-amino-n-caproyl)fortimicin B] as a starting material:

Mass spectrum m/e 461 (M⁺), 444, 348, 330, 320, 302, 271, 235, 207, 189, 143, 126, 114, 97, 86.

Sulfate $[\alpha]^{23°}_D = +74.9°$ (c=1.0, water).

Elemental analysis as $C_{21}H_{43}N_5O_6.2H_2SO_4.C_2H_5OH.2H_2O$: Found: C 37.20, H 7.62, N 9.45, Calculated: C 37.34, H 7.76, N 9.47.

From these physical properties, the compound was identified as 4-N-(ε-amino-n-caproyl)fortimicin B.

EXAMPLE 16

In this example, the solid residue {1,2',6'-tri-N-benzyloxycarbonyl-[4-N-(O-benzylglycolyl)fortimicin B]} obtained in Example 8 was dissolved in 10 ml of 0.1 N hydrochloric acid method of solution and 40 mg of 10% palladium-charcoal was added thereto. Then, hydrogen gas was bubbled through the reaction mixture at room temperature under atmospheric pressure for 8 hours. After completion of the hydrogenation reaction, the catalyst was removed by filtration, and the solvent in the filtrate was removed under reduced pressure. The resulting concentrate, dissolved in 5 ml of water, was charged into a column packed with 15 ml of Amberlite CG-50 (NH₄⁺ form) after adjusting the resulting solution to pH 6 using 1 N sodium hydroxide. After charging, 40 ml of water was used for washing the column, and then, elution was carried out with 0.2 N aqueous ammonia. The eluate was taken in 5 ml fractions. Fractions Nos. 8–14 were combined in which fractions are contained the compounds having an Rf 0.46 in solvent system A in Table 2. These fractions were concentrated to obtain 154 mg of a white powder. From Mass spectrum data, m/e 406 (M⁺), 389, 331, 247, 235, 207, 143, 126, 97, 86.

the product was identified as 4-N-glycolyl-fortimicin B.

In 2 ml of water, 103 mg (0.25 millimole) of the 4-N-glycolylfortimicin B was dissolved and adjusted to pH 2 with 5 N sulfuric acid. The resulting solution was added dropwise to 20 ml of ethanol and after filtration of the resulting precipitate, 91 mg (0.16 millimole) of 4-N-glycolylfortimicin B sulfate was obtained.

Sulfate $[\alpha]^{23°}_D = +89.3°$ (c=1.0, water).

Elemental analysis as $C_{17}H_{34}N_4O_7.1.5H_2SO_4.C_2H_5OH.H_2O$: Found: C 36.70, H 7.44, N 8.93. Calculated: C 36.95, H 7.34, N 9.07.

EXAMPLE 17

In this example, 1.22 grams of tetra-N-benzyloxycarbonyl-(4-N-glycylglycylfortimicin B) obtained in Example 9 was dissolved in 35 ml of 0.2 N hydrochloric acid-method solution, and about 50 mg of 10% palladium-charcoal was added thereto. Then, hydrogen gas was bubbled through the reaction mixture at room temperature under atmospheric pressure for 16 hours. After completion of the hydrogenation reaction, the catalyst was removed by filtration, and the solvent in the filtrate was removed under reduced pressure. The resulting concentrate, dissolved in 10 ml of water, and adjusted to pH 6 using 1 N sodium hydroxide, was charged into a column packed with 30 ml of Amberlite CG-50 (NH₄⁺ form). After charging, 150 ml of water was used for washing the column, and then, elution was carried out with 0.3 N aqueous ammonia. The eluate was taken in 5 ml fractions. Fractions Nos. 13–24 were combined in which fractions are contained the compounds having an Rf 0.42 in solvent system A in Table 2. These fractions were concentrated to obtain 514 mg of white powder.

In 2 ml of water, 100 mg (0.25 millimole) of the compound thus obtained was dissolved and adjusted to pH 2 with 5 N sulfuric acid. The resulting solution was added dropwise to 20 ml of ethanol and after filtration of the resulting precipitate, 123 mg of white powder was obtained. Physical properties of the compound are shown below.

$[\alpha]^{25°}_D = +70.1°$ (c=1.0, water).

Elemental analysis as $C_{19}H_{38}N_6O_7 \cdot 2H_2SO_4 \cdot C_2H_5OH \cdot 2H_2O$: Found: C 33.27, H 7.11, N 10.81. Calculated: C 33.24, H 7.17, N 11.07.

From these physical properties, the compound was identified as 4-N-glycylglycylfortimicin B sulfate. Yield 78%.

EXAMPLE 18

In this example, 100 mg (0.19 millimole) of tetra-N-benzyloxycarbonyl {4-N-[L-(−)-γ-amino-α-hydroxybutyryl]fortimicin B} was dissolved in 10 ml of 0.1 N hydrochloric acid-methanol solution and about 10 mg of 10% palladium-charcoal was added thereto. Then, hydrogen gas was bubbled through the reaction mixture at room temperature under atmospheric pressure for 7 hours. After completion of the hydrogenation reaction, the catalyst was removed by filtration and the solvent in the filtrate was removed under reduced pressure to obtain 62 mg (0.14 millimole) of 4-N-[L-(−)-γ-amino-α-hydroxybutyryl]fortimicin B hydrochloride.

EXAMPLE 19

In this example, 2.0 grams (4.9 millimoles) of fortimicin A obtained by a similar manner as in Example 14 was suspended in 200 ml of tetrahydrofuran and 2.0 grams (53.0 millimoles) of lithium aluminum hydride was added thereto. The resulting reaction mixture was heated at a reflux temperature with stirring for 46 hours. After the completion of the reaction, the reaction mixture was cooled to room temperature and 30 ml of ethyl acetate was added in drops to decompose the excess lithium aluminum hydride. The ethyl acetate was removed under reduced pressure. To the resulting residue, 50 ml of water was added and the insolubles in the resulting mixture were removed by filtration. The filtrate and water used for washing the filtrate were combined. The solvent of the combined solution was removed under reduced pressure and then 200 ml of an aqueous saturated barium hydroxide solution was added to the concentrate, and the solution was heated under reflux for one hour.

The resulting solution was allowed to stand to cool, and then was neutralized by adding dry ice. Then, the solution was filtered, and the filtrate was charged into a column packed with 100 ml of Amberlite CG-50 (NH4+ form). After charging, 400 ml of water and 600 ml of 0.3 N aqueous ammonia were used for washing the column, and then elution was carried out with 0.5 N aqueous ammonia. An eluate was taken in 20 ml fractions. Fraction Nos. 6-20 were combined, in which fractions are contained the compounds having an Rf value of 0.41 in solvent system A in Table 2. These fractions were concentrated to obtain 608 mg of white powder. Physical properties of the compound are shown below.

Mass spectrum m/e 392 (M+ +1), 341, 282, 278, 250, 143, 126.

PMR (deuterium oxide): δ(ppm) 1.02 (3H,d), 1.2-1.9 (4H,m), 2.38 (3H,s), 2.4 (1H,br), 2.70 (4H,s), 2.76 (1H,m), 3.09 (1H,q), 3.16 (1H,t), 3.40 (3H,s), ~3.5 (1H,br), 3.74 (1H,t), 3.85 (1H,q), 4.06 (1H,q), 4.16 (1H,q), 4.92 (1H,d).

CMR (deuterium oxide), δ(ppm): 18.6, 27.0, 27.3, 39.2, 40.6, 50.3, 50.5, 54.9, 57.5, 58.0, 60.7, 71.3, 71.8, 75.1, 76.9, 80.6, 100.6.

From the foregoing data, the compound was identified as 4-N-(2-aminoethyl)fortimicin B. Yield 32.7%.

In 2 ml of water, 390 mg (1.0 millimole) of 4-N-(2-aminoethyl)fortimicin B was dissolved and adjusted to pH 2 with 5 N sulfuric acid. The resulting solution was added dropwise to 20 ml of ethanol and after filtration of the resulting precipitate, 637 mg (0.91 millimole) of 4-N-(2-aminoethyl)fortimicin B sulfate was obtained.

$[\alpha]^{25°}_D = +77.8°$ (c=1.0, water).

Elementary analysis as $C_{17}H_{37}N_5O_5 \cdot 2\frac{1}{2}H_2SO_4 \cdot C_2H_5OH \cdot H_2O$: Found: C 32.55, H 7.19, N 9.93; Calculated: C 32.56, H 7.21, N 9.99.

EXAMPLE 20

In this example, 200 mg (0.49 millimole) of fortimicin A obtained in a similar manner as in Example 14 was suspended in 10 ml of tetrahydrofuran and 10 ml of a tetrahydrofuran solution containing 1 mole/l of diborane (10.0 millimoles). Then, the resulting reaction mixture was stirred at room temperature for two hours. After the completion of the reaction, 1 ml of water was added thereto in order to decompose excess diborane. The resulting reaction mixture was concentrated to dryness under reduced pressure. Then 20 ml of 80% hydrazine solution was added to the residue, and the reaction mixture was heated under reflux for 16 hours and then was concentrated to dryness under reduced pressure. The resulting concentrate, dissolved in 10 ml of water and ajusted to pH 6 with 1 N hydrochloric acid, was charged into a column packed with 10 ml of Amberlite CG-50 (NH4+ form).

After charging, 50 ml of water and 90 ml of 0.3 N aqueous ammonia were used for washing the column, and then, elution was carried out with 0.5 N aqueous ammonia. The elute was taken in 2 ml fractions. Fractions Nos. 9-36 were combined and concentrated to obtain 146 mg of white powder. Physicochemical properties of the powder were identical with the compound obtained in Example 18. The compound thus obtained was 4-N-(2-aminoethyl)fortimicin B. Yield 75.5 %.

EXAMPLE 21

In this example, the procedures of Example 20 were repeated, except that 0.5 millimole each of 4-N-acyl (or substituted acyl)fortimicin B shown in the following Table D was used in place of fortimicin A.

Table D

| Example No. | Compound used |
|---|---|
| 21-1 | 4-N-acetylfortimicin B |
| 21-2 | 4-N-propionylfortimicin B |
| 21-3 | 4-N-(n-butyryl)fprtimicin B |
| 21-4 | 4-N-(n-valeryl)fortimicin B |
| 21-5 | 4-N-(β-alanyl)fortimicin B |
| 21-6 | 4-N-(γ-amino-n-butyryl)fortimicin B |
| 21-7 | 4-N-(δ-amino-n-valeryl-fortimicin B |
| 21-8 | 4-N-(ε-amino-n-caproyl)fortimicin B |
| 21-9 | 4-N-glycolylfortimicin B |
| 21-10 | 4-N-glycylglycylfortimicin B |

It was identified from the respective physical properties thus that the following products were obtained.

(1) name of the compound, (2) amount, (3) yield and (4) physical properties of the powder thus obtained are given below.

EXAMPLE 21-1

(1) 4-N-ethyl fortimicin B
(2) 125 mg (0.33 millimole)
(3) 66%
(4) Mass spectrum: m/e 377 (M+ +1), 376 (M+), 359, 344, 327, 314, 299, 286, 273, 263, 235, 217, 215, 202, 143, 114.

PMR (deuterium oxide): δ(ppm): 1.02 (3H,d), 1.08 (3H,t), 1.2–1.9 (4H,m), 2.40 (3H,s), 2.6–3.0 (4H,m), 3.12 (1H,q), 3.18 (1H,t), 3.42 (3H,s), 3.40 (1H,br), 3.74 (1H,t), 3.85 (1H,q), 4.08 (1H,q), 4.17 (1H,t), 4.92 (1H,d).

EXAMPLE 21-2

(1) 4-N-(n-propyl)fortimicin B
(2) 136 mg (0.35 millimole)
(3) 70%
(4) Mass spectrum: m/e 390 (M+), 373, 361, 358, 344, 341, 328, 287, 277, 249, 231, 229, 219, 202, 143, 128.

EXAMPLE 21-3

(1) 4-N-(n-butyl)fortimicin B
(2) 137 mg (0.34 millimole)
(3) 68%
(4) Mass spectrum: m/e 404 (M+), 372, 361, 342, 301, 291, 286, 263, 219, 202, 143, 142.

EXAMPLE 21-4

(1) 4-N-(n-pentyl)fortimicin B
(2) 167 mg (0.40 millimole)
(3) 80%
(4) Mass spectrum: m/e 419 (M+ +1), 418 (M+), 386, 369, 361, 356, 344, 331, 326, 315, 305, 277, 259, 219, 207, 202, 156, 143.

EXAMPLE 21-5

(1) 4-N-(3-aminopropyl)fortimicin B
(2) 117 mg (0.29 millimole)
(3) 58%
(4) Mass spectrum: m/e 406 (M+ +1), 373, 338, 328, 292, 264, 231, 228, 219, 202, 196, 172, 143, 126, 100, 89, 58.

PMR (deuterium oxide): δ(ppm): 1.04 (3H,d), 1.2–1.9 (6H,m), 2.42 (3H,s), 2.5–3.0 (6H,m), 3.14 (1H,q), 3.20 (1H,t), 3.44 (3H,s), ~3.4 (1H,m), 3.79 (1H,t), 3.88 (1H,q), 4.06 (1H,q), 4.18 (1H,t), 4.94 (1H,d).

Sulfate: $[\alpha]^{23°}_D = +71.9°$ (c=1.0, water).

Elementary analysis as $C_{18}H_{39}N_5O_5 \cdot 2.5H_2SO_4 \cdot C_2H_5OH \cdot 2H_2O$: Found: C 32.04, H 7.80, N 8.99, Calculated: C 31.99, H 7.52, N 9.33.

EXAMPLE 21-6

(1) 4-N-(4-aminobutyl)fortimicin B
(2) 75 mg (0.18 millimole)
(3) 35%
(4) Mass spectrum: m/e 240 (M+ +1), 419 (M+), 370, 352, 342, 306, 278, 219, 210, 207, 186, 157, 143, 103, 72.

PMR (deuterium oxide): δ(ppm): 1.02 (3H,d), 1.2–1.9 (8H,m), 2.42 (3H,s), 2.5–3.0 (6H,m), 3.06 (1H,t), 3.09 (1H,t), 3.44 (3H,s), ~3.4 (1H,m), 3.78 (1H,q), 3.86 (1H,q), 4.04 (1H,q), 4.16 (1H,t), 4.93 (1H,d).

Sulfate $[\alpha]^{23°}_D = +72.8°$ (c=1.0, water).

Elementary analysis as $C_{19}H_{41}N_5O_5 \cdot 2.5H_2SO_4 \cdot C_2H_5OH \cdot 3H_2O$: Found: C 32.74, H 7.69, N 8.91. Calculated: C 32.98, H 7.64, N 9.16.

EXAMPLE 21-7

(1) 4-N-(5-aminopentyl)fortimicin B
(2) 22 mg (0.05 millimole)
(3) 10%
(4) Mass spectrum: m/e 434 (M+ +1), 433 (M+), 384, 366, 320, 292, 271, 224, 219, 171, 143, 126, 117, 89, 86.

PMR (deuterium oxide): δ(ppm): 1.04 (3H,d), 1.2–1.9 (10H,m), 2.44 (3H,s), 2.5–3.0 (6H,m), 3.14 (1H,t), 3.20 (1H,t), 3.40 (1H,m), 3.44 (3H,s), 3.80 (1H,t), 3.84 (1H,q), 4.07 (1H,q), 4.16 (1H,t), 4.96 (1H,d).

Sulfate $[\alpha]^{23°}_D = +67.3°$ (c=1.0, water).

EXAMPLE 21-8

(1) 4-N-(6-aminohexyl)fortimicin B
(2) 147 mg (0.33 millimole)
(3) 66%
(4) Mass spectrum: m/e 448 (M+ +1), 447 (M+), 429, 402, 398, 380, 370, 361, 334, 320, 306, 288, 285, 238, 222, 219, 199, 185, 143, 131, 126, 112, 98.

PMR (deuterium oxide): δ(ppm): 1.02 (3H,s), 1.2–1.9 (12H,m), 2.40 (3H,s), 2.5–3.0 (6H,m), 3.12 (1H,t), 3.16 (1H,t), 3.43 (3H,s), ~3.4 (1H,m), 3.73 (1H,t), 3.84 (1H,q), 4.04 (1H,q), 4.14 (1H,t), 4.86 (1H,d).

Sulfate $[60]^{23°}_D = +71.3°$ (c=1.0, water).

Elementary analysis as $C_{21}H_{45}N_5O_5 \cdot 2.5H_2SO_4 \cdot C_2H_5OH \cdot 2H_2O$: Found: C 35.74, H 7.77, N 8.78; Calculated: C 35.65, H 7.80, N 9.04.

EXAMPLE 21-9

(1) 4-N-(2-hydroxyethyl)fortimicin B
(2) 106 mg (0.27 millimole)
(3) 54%
(4) Mass spectrum: m/e 393 (M+ +1), 374, 361, 344, 331, 279, 259, 251, 235, 219, 207, 202, 143, 130, 126, 100, 97, 86.

PMR (deuterium oxide): δ(ppm): 1.01 (3H,d), 1.2–1.9 (4H,m), 2.44 (3H,s), 2.78 (2H,t), 2.4–3.0 (2H,m), 3.14 (1H,t), 3.18 (1H,t), ~3.4 (1H,m), 3.44 (1H,s), 3.64 (2H,t), 3.76 (1H,t), 3.87 (1H,q), 4.06 (1H,q), 4.16 (1H,t), 4.96 (1H,d).

Sulfate $[\alpha]^{24°}_D = +77.4°$ (c=1.0, water).

EXAMPLE 21-10

(1) 4-N-[2-(2-aminoethyl)aminoethyl]fortimicin B
(2) 121 mg (0.28 millimole)
(3) 57%
(4) Mass spectrum: m/e 435 (M+ +1), 417, 404, 361, 344, 219, 143, 126, 100.

PMR (deuterium oxide): δ(ppm): 1.00 (3H,d), 1.2–1.9 (4H,m), 2.40 (3H,s), 2.6–3.0 (10H,m), 3.08 (1H,q), 3.16 (1H,t), 3.40 (3H,s), −3.4 (1H,m), 3.74 (1H,t), 3.86 (1H,q), 4.08 (1H,q), 4.16 (1H,t), 4.94 (1H,d).

EXAMPLE 22

In this example, 151 mg (0.20 millimole) of 1,2',6'-tri-N-benzyloxycarbonylfortimicin B was dissolved in 10 ml of ethanol and 0.02 ml (0.25 millimole) of ethyl iodine was added thereto. The reaction mixture was heated under reflux for 17 hours and thereafter was concentrated to dryness under reduced pressure. The resulting concentrate was dissolved in 20 ml of ethylacetate and 10 ml each of an aqueous 5% sodium bicarbonate solution and water was added thereto. After shaking, the ethyl acetate layer separated by using a funnel was dried with anhydrous sodium sulfate, and then concentrated to dryness under reduced pressure.

The resulting solid residue was dissolved in a small amount of chloroform, and the chloroform solution was charged into a column packed with 25 g of silica gel [Kieselgel 60]. In this step, elution was carried out with a mixed solvent of methanol and chloroform (2:98 by volume) and the elute was taken in 6 ml fractions. Fractions Nos. 29–54 were combined in which fractions are contained the compounds having an Rf value 0.49 in solvent system C in Table 2. These fractions were concentrated to dryness under reduced pressure whereby 30 mg of white powder was obtained.

Physical properties of the compound are shown below.

PMR (methanol-d$_4$): δ(ppm): 1.08 (3H,t), 1.02 (3H,d), 1.2–1.9 (4H,m), 2.48 (3H,s), 2.90 (2H,q), 3.43 (3H,s), 5.02 (6H,s), 7.28 (15H,s).

From the physical properties above described, the compound was identified as 1,2',6'-tri-N-benzyloxycarbonyl-4-N-ethylfortimicin B. Yield 19%.

EXAMPLE 23

In this example, 942 mg (1.0 millimole) of tetra-N-benzyloxycarbonylfortimicin A obtained by a similar method as described in Example 6 was dissolved in 10 ml of tetrahydrofuran and 10 ml of diborane in tetrahydrofuran (concentration: 1 mole/l) was added thereto. Then, the resulting reaction mixture was stirred for 2 hours at room temperature.

After the completion of the reaction, 1 ml of water was added to the reaction mixture in order to decompose any excess diborane and the reaction mixture was concentrated to dryness under reduced pressure. The resulting concentrate was dissolved in 20 ml of ethylacetate and then 10 ml of 5% aqueous sodium bicarbonate was added thereto. After shaking the resulting mixture, the ethyl acetate layer was washed twice with 10 ml of water. The ethyl acetate layer was then separated and dried with anhydrous sodium sulfate and concentrated to dryness under reduced pressure. The resulting concentrate, dissolved in a small portion of chloroform, was charged into a column packed with 40 g of a silica gel (Kieselgel 60).

Elution was carried out with a mixed solvent of methanol-chloroform (2:98 by volume), and the elute was taken in 6 ml fractions. Fractions Nos. 6–19 were combined in which fractions the compound having an Rf value of 0.70 in solvent system C in Table 2 and these fractions were concentrated under reduced pressure to obtain 318 mg of white powder.

Physical properties of the compound are shown below.

PMR spectrum (methanol-d$_4$): δ(ppm): 1.08 (3H,d), 1.2–1.9 (4H,m), 2.35 (3H,s), 3.34 (3H,s), 5.02 (8H,s), 7.28 (20H,s).

From the data above described, the compound was identified as tetra-benzyloxycarbonyl-[4-N-(2-aminoethyl)fortimicin B].

An additional elution was carried out with 250 ml of a mixed solvent of methanol-chloroform (1:9 by volume) to obtained fractions in which the compound having an Rf value of 0.15 in solvent system C in Table 2. The fractions were concentrated under reduced pressure to obtain 266 mg of white powder.

The physical properties are shown below:

PMR spectrum (methanol-d$_4$): δ(ppm): 1.08 (3H,d), 1.2–1.9 (4H,m), 2.37 (3H,s), 2.42 (3H,s), 3.40 (3H,s), 5.08 (6H,s), 7.28 and 7.34 (15H total; s, respectively).

From the data above described, the compound was identified as 1,2',6'-tri-N-benzyloxy-carbonyl-4-N-(2-methylaminoethyl)fortimicin B.

EXAMPLE 24

In this example, 30 mg (0.039 millimole) of 1,2',6'-tri-N-benzyloxycarbonyl-(4-N-ethyl)fortimicin B obtained in Example 22 was dissolved in 10 ml of 0.1 N hydrochloric acid-methanol solution and about 2 mg of palladium charcoal was added thereto. Then, hydrogen gas was bubbled through the reaction mixture at room temperature under atmospheric pressure for 8 hours. After the completion of the hydrogenation reaction, the catalyst was removed by filtration. The solvent of the filtrate was removed under reduced pressure. As a result, 21 mg of white powders were obtained.

Physical properties of thus obtained compound were identical with those of the compound obtained in Example 21-1, and it was identified that the compound was 4-N-ehtylfortimicin B hydrochloride. Yield 97%.

EXAMPLE 25

In this example, 310 mg (0.33 millimole) of tetra-N-benzyloxycarbonyl-[4-N-(2-aminoethyl)fortimicin B] obtained in Example 23 was dissolved in 20 ml of 0.1 N hydrochloric acid-methanol solution and about 20 mg of 10% palladium-charcoal was added thereto. Then, hydrogen gas was bubbled through the reaction mixture, at room temperature under atmospheric pressure for 18 hours. After the completion of the hydrogenation reaction, the catalyst was removed by filtration. The solvent of the filtrate was removed under reduced pressure. The resulting concentrate, dissolved in 5 ml of water, was changed into a column packed with Amberlite CG-50 (NH$_4^+$ form) after being adjusted to pH 6 using 1 N sodium hydroxide. After charging, 50 ml of water and 90 ml of 0.3 N aqueous ammonia was used for washing the column, and then elution was carried out with 0.5 N aqueous ammonia. The eluate was taken in 5 ml fractions. Fractions Nos. 6–43 were combined in which fractions are contained the compound having an Rf 0.4 in solvent system A in Table 2. These fractions were concentrated to obtained 123 mg of white powder.

Physical properties of thus obtained compound were identical with those of the compound obtained in Example 19, and was identified as 4-N-(2-aminoethyl)-fortimicin B. Yield 94%.

EXAMPLE 26

In this example, 261 mg (0.32 millimole) of 1,2',6'-tri-N-benzyloxycarbonyl-4-N-(2-methylaminoethyl)fortimicin B obtained in Example 23 was dissolved in 15 ml of 0.1 N hydrochloric acid-methanol solution and about 20 mg of 10% palladium-charcoal was added thereto. Then, hydrogen gas was bubbled through the reaction mixture at room temperature under atmospheric pressure for 17 hours. After completion of the hydrogenation reaction, the catalyst was removed by filtration and the solvent of the filtrate was removed under reduced pressure. The resulting concentrate, dissolved in 5 ml of water and adjusted to pH 6 with 1 N sodium hydroxide, was charged into a column packed with 10 ml of Amberlite CG-50 (NH$_4^+$ form). After charging, 50 ml of water and 90 ml of 0.3 N aqueous ammonia was used for washing the column, and then, elution was carried out with 0.5 N aqueous ammonia. The eluate was taken in 5 ml fractions. Fractions Nos. 6–18 were combined in which fractions are contained the compounds having an Rf 0.43 in solvent system A in Table 2. These fractions were concentrated to obtain 92 mg of white powder.

Physical properties of thus obtained compound are shown below.

Mass spectrum: m/e 406 (M$^+$+1), 375, 355, 296, 292, 264, 219, 143, 126, 100.

PMR (deuterium oxide): δ (ppm): 1.02 (3H,d), 1.2–1.9 (4H,m), 2.12 (3H,s), 2.41 (3H,s), 2.5–3.0 (6H,m), 3.08 (1H,q), 3.16 (1H,t), ~3.4 (1H,m), 3.41 (3H,s), 3.73 (1H,t), 3.84 (1H,q), 4.05 (1H,q), 4.15 (1H,t), 4.92 (1H,d).

CMR (deuterium oxide): δ (ppm): 18.6, 27.0, 27.3, 35.6, 40.6, 49.1, 50.4, 50.5, 54.7, 54.9, 57.4, 60.5, 71.3, 71.8, 75.2, 76.7, 80.5, 100.6.

Sulfate $[\alpha]_D^{25°}$ = +68.0° (c=1.0, water).

From these data above described, it was identified that the compound was 4-N-[2-(methylaminoethyl)]fortimicin B.

EXAMPLE 27

The same reaction were carried out in a similar manner as in Example 10 using a N-benzyloxycarbonyl derivatives shown in Table C to obtain the compounds (IV) shown in Table C, in which reaction equal molar amount of N-benzyloxycarbonyl derivatives shown in Table C were used in place of L-(−)-γ-benzyloxycarbonylamino-α-hydroxybutyric acid.

Table C

| Compound used in place of L-(-)-γ-benzyloxy-carbonylamino-α-hydroxy-butyric acid | Compound (IV) |
| --- | --- |
| DL-γ-benzyl-oxycarbonylamino-α-hydroxybutyric acid | tetra-N-benzyloxycarbonyl-[4-(DL-γ-amino-α-hydroxy-butyryl)fortimicin B] |
| L-β-benzyl-oxycarbonylamino-α-hydroxypropionic acid | tetra-N-benzyloxycarbonyl-[4-(L-β-amino-α-hydroxy-propionyl)fortimicin B] |
| L-δ-benzyl-oxycarbonylamino-α-hydroxyvaleric acid | tetra-N-benzyloxycarbonyl-[4-(L-δ-amino-α-hydroxyvaleryl)-fortimicin B] |

EXAMPLE 28

Similar preparations were repeated in a similar manner as Example 23, using tetra-N-benzyloxycarbonyl-(4-N-substituted acylfortimicin B) derivatives shown in Table E in place of tetra-N-benzyloxycarbonylfortimicin A to obtain the compounds (V) in Table E.

Table E

| Compound used in place of tetra-N-benzyloxycarbonyl-fortimicin A | Compound (V) |
| --- | --- |
| tetra-N-benzyloxycarbonyl-[4-N-(Lγ-amino-α-hydroxy-butyryl)fortimicin B | tetra-benzyloxycarbonyl-{4-N-[(S)-4-amino-2-hydroxy-butyl]fortimicin B} and tri-N-benzyloxycarbonyl-{4-N-[(S)-4-methylamino-2-hydroxybutyl]fortimicin B} |
| tetra-N-benzyloxycarbonyl-[4-N-(DL-γ-amino-α-hydroxy-butyryl)fortimicin B | tetra-N-benzyloxycarbonyl-{4-N-[(R,S)-4-amino-2-hydroxy-butyl]fortimicin B} and tri-N-benzyloxycarbonyl-{4-N-[(R,S)-4-methylamino-2-hydroxybutyl]fortimicin B} |
| tetra-N-benzyloxycarbonyl-[4-N-(Lβ-amino-α-hydroxy-propionyl)fortimicin B] | tetra-N-benzyloxycarbonyl-{4-N-[(S)-3-amino-2-hydroxy-propyl]fortimicin B} and tri-N-benzyloxycarbonyl-{4-N-[(S)-3-methylamino-2-hydroxypropyl]fortimicin B} |
| tetra-N-benzyloxycarbonyl-[4-N-(L-δ-amino-α-hydroxy-valeryl)fortimicin B] | tetra-N-benzyloxycarbonyl-{4-N-[(S)-5-amino-2-hydroxy-pentyl]fortimicin B} |

EXAMPLE 29

Similar preparations were repeated in a similar manner as in Example 25, except that tetra- or tri-N-benzyloxycarbonyl-(4-N-substituted alkylfortimicin B) derivatives shown in the following Table F were used in place of tetra-N-benzyloxycarbonyl-[4-N-(2-aminoethyl)fortimicin B] in Example 25.

Table F

| Example No. | Compound used |
| --- | --- |
| 29-1 | tetra-N-benzyloxycarbonyl-{4-N-[(S)-4-amino-2-hydroxy-butyl]fortimicin B} |
| 29-2 | tri-N-benzyloxycarbonyl-{4-N-[(S)-4-methylamino-2-hydroxybutyl]fortimicin B} |
| 29-3 | tetra-N-benzyloxycarbonyl-{4-N-[(R,S)-4-amino-2-hydroxy-butyl]fortimicin B} |
| 29-4 | tri-N-benzyloxycarbonyl-{4-N-[(R,S)-4-methylamino-2-hydroxybutyl]fortimicin B} |
| 29-5 | tetra-N-benzyloxycarbonyl-{4-N-[(S)-3-amino-2-hydroxy-propyl]fortimicin B} |
| 29-6 | tri-N-benzyloxycarbonyl-{4-N-[(S)-3-methylamino-2-hydroxypropyl]fortimicin B} |
| 29-7 | tetra-N-benzyloxycarbonyl-{4-N-[(S)-5-amino-2-hydroxy-pentyl]fortimicin B} |

It was identified from the respective physical properties thus obtained that the products thus obtained were the compounds as mentioned.

(1) name of the compounds and (2) physical properties of the powders thus obtained are given below.

EXAMPLE 29-1

(1) 4-N-[(S)-4-amino-2-hydroxybutyl]fortimicin B (2) Mass spectrum: m/e 436 (M$^+$+1), 417, 400, 387, 361, 344, 330, 322, 294, 259, 245, 235, 219, 207, 202, 143, 126, 119, 100.

CMR (deuterium oxide): δ(ppm): 18.6, 27.0, 27.3, 37.7, 38.2, 40.4, 50.3, 50.5, 54.9, 57.3, 61.5, 67.7, 70.1, 71.7, 75.2, 76.5, 80.5, 100.6.

Sulfate $[\alpha]_D^{23°}$ = +78.6° (c=1.0, water).

Elemental analysis as $C_{19}H_{41}N_5O_6 \cdot 2.5H_2SO_4 \cdot C_2H_5OH \cdot 3H_2O$; Found: C 32.62, H 7.84, N 8.64; Calculated: C 32.30, H 7.49, N 8.97.

EXAMPLE 29-2

(1) 4-N-[(S)-4-methylamino-2-hydroxybutyl]fortimicin B (2) Mass spectrum: m/e 450 (M$^+$+1), 431, 400, 388, 374, 370, 361, 344, 336, 330, 308, 259, 245, 219, 207, 202, 143, 133, 126, 100.

CMR (deuterium oxide): δ(ppm): 18.6, 27.1, 27.3, 34.4, 35.4, 40.4, 48.0, 50.3, 50.5, 54.9, 57.3, 61.5, 61.8, 67.4, 68.0, 70.8, 71.7, 75.2, 76.5, 80.5, 100.6.

Sulfate $[\alpha]_D^{23°} = +77.5°$ (c=1.0, water).

Elemental analysis as $C_{20}H_{43}N_5O_6 \cdot 2.5H_2SO_4 \cdot C_2H_5OH \cdot H_2O$; Found: C 34.82, H 7.44, N 9.22; Calculated: C 34.65, H 7.65, N 8.93.

EXAMPLE 29-3

(1) 4-N-[(R,S)-4-amino-2-hydroxybutyl]fortimicin B.

(2) Mass spectrum: m/e 436 (M++1), 417, 400, 387, 361, 344, 330, 322, 294, 259, 245, 235, 219, 207, 202, 143, 126, 119, 100.

Sulfate $[\alpha]_D^{24°} = +92.5°$ (c=0.2, water).

Elemental analysis as $C_{19}H_{41}N_5O_6 \cdot 2.5H_2O \cdot C_2H_5OH \cdot 4H_2O$; Found: C 31.44, H 7.98, N 8.48; Calculated: C 31.57, H 7.57, N 8.76.

EXAMPLE 29-4

(1) 4-N-[(R,S)-4-methylamino-2-hydroxybutyl]fortimicin B.

(2) Mass spectrum: m/e 450 (M++1), 431, 400, 388, 374, 370, 361, 344, 336, 330, 308, 259, 245, 219, 207, 202, 143, 133, 126, 100.

EXAMPLE 29-5

(1) 4-N-[(S)-3-amino-2-hydroxypropyl]fortimicin B.

(2) Mass spectrum: m/e 422 (M++1), 403, 391, 361, 344, 330, 308, 280, 259, 249, 231, 219, 207, 202, 159, 143, 126, 105, 100.

Sulfate $[\alpha]_D^{23°} = +86.5°$ (c=0.2, water).

Elemental analysis as $C_{18}H_{39}N_5O_6 \cdot 2.5H_2SO_4 \cdot C_2H_5OH \cdot H_2O$; Found: C 32.85, H 6.93, N 9.23; Calculated: C 32.87, H 7.17, N 9.58.

EXAMPLE 29-6

(1) 4-N-[(S)-3-methylamino-2-hydroxypropyl]fortimicin B.

(2) Mass spectrum: m/e 436 (M++1), 417, 403, 391, 373, 361, 344, 330, 322, 313, 294, 219, 207, 202, 143, 126, 119, 99.

Sulfate $[\alpha]_D^{23°} = +74.5°$ (c=0.2, water).

Elemental analysis as $C_{19}H_{41}N_5O_6 \cdot 2.5H_2SO_4 \cdot C_2H_5OH \cdot 3H_2O$; Found: C 32.48, H 7.40, N 8.71; Calculated: C 32.30, H 7.49, N 8.97.

EXAMPLE 29-7

(1) 4-N-[(S)-5-amino-2-hydroxypentyl]fortimicin B.

(2) Mass spectrum: m/e 450 (M++1), 431, 387, 361, 344, 336, 330, 313, 308, 259, 219, 207, 202, 143, 133, 126, 100.

Sulfate $[\alpha]_D^{24°} = +75.5°$ (c=0.2, water).

Elemental analysis as $C_{20}H_{43}N_5O_6 \cdot 2.5H_2SO_4 \cdot C_2H_5OH \cdot H_2O$; Found: C 34.78, H 7.72, N 8.98; Calculated: C 34.82, H 7.44, N 9.22.

$ED_{50}$ and $LD_{50}$ of some of the present compounds are shown below.

(1) $ED_{50}$

In this experiment, one group consisting of five ddY-strain mice is used. The microorganisms shown below are inoculated into each animal. One hour after the inoculation, test compounds dissolved in distilled water for injection are injected intraperitoneally to test animals by one shot. The test animals are observed one week after the injection, and the $ED_{50}$ is calculated according to the method of Behrens-Kärber. The obtained results are shown below.

| No. of test compound | Test compound | $ED_{50}$ (mg/kg) KP*[1] | $ED_{50}$ (mg/kg) EC*[2] |
|---|---|---|---|
| 2 | Fortimicin A sulfate | 2.06 | 5.06 |
| 27 | 4-N-[(S)-4-amino-2-hydroxybutyl]fortimicin B sulfate | 1.88 | 2.81 |

*[1]KP means *Klebsiella pneumoniae* 8045. $1.3 \times 10^5$ cells are inoculated into each mouse.

*[2]EC means *Escherichia coli* Juhl. $2.1 \times 10^4$ cells are inoculated into each mouse.

(2) $LD_{50}$

In this experiment, one group consisting of five ddY-strain mice is used. Test compounds dissolved in 0.2 ml of distilled water for injection are injected intravenously into each animal in 10 seconds. The $LD_{50}$ is calculated according to the method of Behrens-Kärber. The obtained results are shown below.

| No. of test compound | Test compound | $LD_{50}$ (mg/kg) |
|---|---|---|
| 2 | Fortimicin A sulfate | 330 |
| 27 | 4-N-[(S)-4-amino-2-hydroxybutyl]fortimicin B sulfate | 135 |

The present invention includes within its scope pharmaceutical compositions comprising, as an active ingredient, at least one of the compounds of this invention which exhibit antimicrobial activity in association with the pharmaceutical carrier or diluent. The compounds of this invention can be administered by oral or parenteral routes of administration, i.e., intramuscular, intravenous, or subcutaneous routes of administration, or rectal administration, and can be formulated in dosage forms suitable for each route of administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides inert diluents, such compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile water, solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredients in the compositions of this invention may be varied; however, it is necessary that the amount of the active ingredients be such that suitable dosage form is obtained. The selected dosage depends upon the desired therapeutical effect, the route of administration and the duration of treatment desired.

What is claimed is:

1. A compound of the formula:

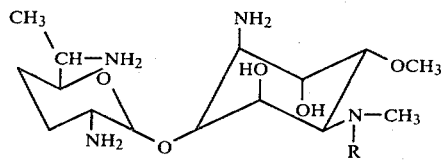

wherein R represents a group selected from

and $-CH_2-R_2$, wherein $R_1$ represents an alkyl group having 2 to 8 carbon atoms an aminoalkyl group having 3 to 8 carbon atoms, a carbamoylamino-alkyl group having 3 to 9 carbon atoms or a hydroxyalkyl group having 1 to 5 carbon atoms, and $R_2$ represents an alkyl group having 1 to 8 carbon atoms, a hydroxylalkyl group having 1 to 5 carbon atoms, an aminoalkyl group having 1 to 8 carbon atoms, an N-alkylaminoalkyl group having 2 to 10 carbon atoms, an aminohydroxyalkyl group having 2 to 8 carbon atoms, an N-substituted aminoalkyl group (wherein the aminoalkyl group has 2 to 5 carbon atoms and the N-substituent is an aminoalkyl group having 1 to 5 carbon atoms) or an N-alkylaminohydroxyalkyl group having 2 to 8 carbon atoms, and the pharmaceutically acceptable non-toxic acid addition salts thereof.

2. A compound of the formula:

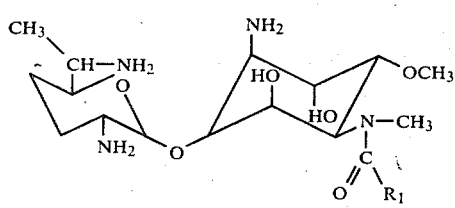

wherein $R_1$ represents an alkyl group having 2 to 8 carbon atoms, an aminoalkyl group having 3 to 8 carbon atoms, a carbamoylamino-alkyl group having 3 to 9 carbon atoms or a hydroxyalkyl group having 1 to 5 carbon atoms and the pharmaceutically acceptable non-toxic acid addition salts thereof.

3. A compound according to claim 2 wherein $R_1$ is $-CH_2-CH_3$.

4. A compound according to claim 2 wherein $R_1$ is $-CH_2-CH_2-CH_3$.

5. A compound according to claim 2 wherein $R_1$ is $-CH_2-CH_2-CH_2-CH_3$.

6. A compound according to claim 2 wherein $R_1$ is $-CH_2-CH_2-CH_2-NH_2$.

7. A compound according to claim 2 wherein $R_1$ is $-CH_2-CH_2-CH_2-CH_2-NH_2$.

8. A compound according to claim 2 wherein $R_1$ is $-CH_2-CH_2-CH_2-CH_2-NH_2$.

9. A compound according to claim 2 wherein $R_1$ is $-CH_2-OH$.

10. A compound of the formula:

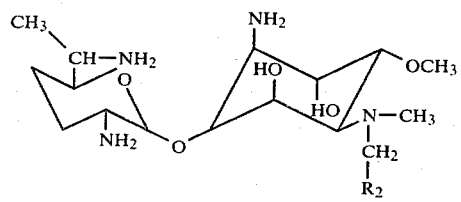

wherein $R_2$ represents an alkyl group having 1 to 8 carbon atoms, an hydroxyalkyl group having 1 to 5 carbon atoms, an aminoalkyl group having 1 to 8 carbon atoms, an N-alkylaminoalkyl group having 2 to 10 carbon atoms, an amino hydroxylalkyl group having 2 to 8 carbon atoms, an N-substituted aminoalkyl group (wherein the aminoalkyl group has 2 to 5 carbon atoms, and the N-substituent is an aminoalkyl group having 1 to 5 carbon atoms) or an N-alkylaminohydroxyalkyl group having 2 to 8 carbon atoms, and the pharmaceutically acceptable non-toxic acid addition salts thereof.

11. A compound according to claim 10 wherein $R_2$ is $-CH_2-NH_2$.

12. A compound according to claim 10 wherein $R_2$ is $-CH_3$.

13. A compound according to claim 10 wherein $R_2$ is $-CH_2-CH_3$.

14. A compound according to claim 10 wherein $R_2$ is $-CH_2-CH_2-CH_3$.

15. A compound according to claim 10 wherein $R_2$ is $-CH_2-CH_2-CH_2-CH_3$.

16. A compound according to claim 10 wherein $R_2$ is $-CH_2-CH_2-NH_2$.

17. A compound according to claim 10 wherein $R_2$ is $-CH_2-CH_2-CH_2-NH_2$.

18. A compound according to claim 10 wherein $R_2$ is $-CH_2-CH_2-CH_2-CH_2-NH_2$.

19. A compound according to claim 10 wherein $R_2$ is $-CH_2-CH_2-CH_2-CH_2-CH_2-NH_2$.

20. A compound according to claim 10 wherein $R_2$ is $-CH_2-OH$.

21. A compound according to claim 10 wherein $R_2$ is $-CH_2-HN-CH_2-CH_2-NH_2$.

22. A compound according to claim 10 wherein $R_2$ is

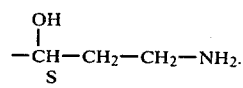

23. A compound according to claim 10 wherein $R_2$ is

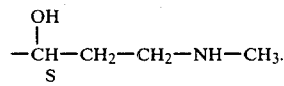

24. A compound according to claim 10 wherein $R_2$ is

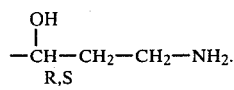

25. A compound according to claim 10 wherein $R_2$ is

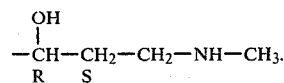

26. A compound according to claim 10 wherein $R_2$ is

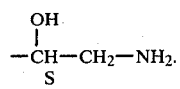

27. A compound according to claim 10 wherein $R_2$ is

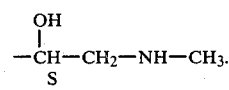

28. A compound according to claim 10 wherein $R_2$ is

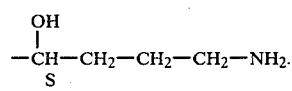

29. A compound according to claim 10 wherein $R_2$ is —CH$_2$—NH—CH$_3$.

30. 1,2',6'-Tri-N-t-butyloxycarbonylfortimicin B.

31. 1,2',6'-Tri-N-t-butyloxycarbonyl-4-N-hydantoylfortimicin B which is 1,2',6'-Tri-N-t-butyloxycarbonyl-fortimicin C.

32. A compound of the formula:

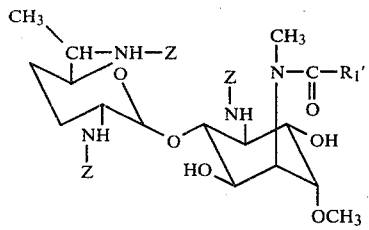

wherein Z represents a benzyloxycarbonyl protecting group and $R_1'$ is an alkyl group having 2 to 8 carbon atoms, a benzyloxycarbonylaminoalkyl group wherein the aminoalkyl group has 3 to 8 carbon atoms, a benzyloxycarbonylaminohydroxyalkyl group wherein the hydroxyalkyl group has 2 to 8 carbon atoms, or a benzyloxyalkyl group having 1 to 5 carbon atoms.

33. A compound according to claim 32 wherein $R_1'$ is —CH$_2$—CH$_3$.

34. A compound according to claim 32 wherein $R_1'$ is —CH$_2$—CH$_2$—CH$_3$.

35. A compound according to claim 32 wherein $R_1'$ is —CH$_2$—CH$_2$—CH$_2$—CH$_3$.

36. A compound according to claim 32 wherein $R_1'$ is

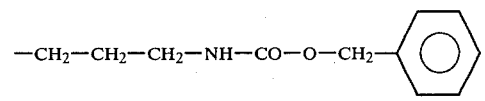

37. A compound according to claim 32 wherein $R_1'$ is

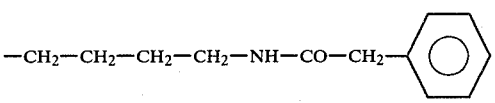

38. A compound according to claim 32 wherein $R_1'$ is

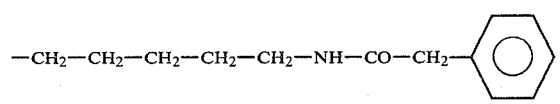

39. A compound according to claim 32 wherein $R_1'$ is

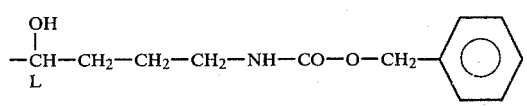

40. A compound according to claim 32 wherein $R_1'$ is

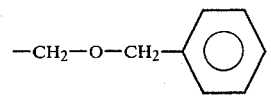

41. A compound of the formula:

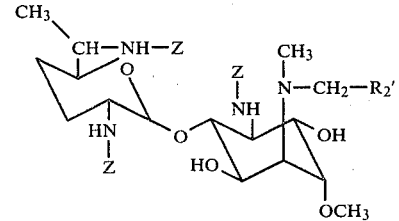

wherein Z represents a benzyloxycarbonyl protecting group and $R_2'$ is an alkyl group having 1 to 8 carbon atoms, a benzyloxycarbonylaminoalkyl group, wherein the aminoalkyl group has 3 to 8 carbon atoms, a benzyloxycarbonylaminohydroxyalkyl group wherein the hydroxyalkyl group has 2 to 8 carbon atoms, or a benzyloxyalkyl group having 1 to 5 carbon atoms.

42. A compound according to claim 41 wherein $R_2'$ is —$CH_3$.

43. A compound according to claim 41 wherein $R_2'$ is

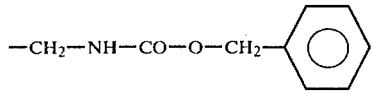

44. A compound according to claim 41 wherein $R_2'$ is —$CH_2$—NH—$CH_3$.

45. A compound according to claim 41 wherein $R_2'$ is

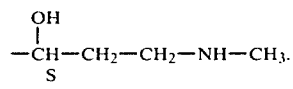

46. A compound according to claim 41 wherein $R_2'$ is

—CH—CH$_2$—CH$_2$—NH—CH$_3$.
  |
  OH
  S

47. A compound according to claim 41 wherein $R_2'$ is

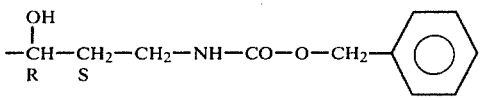
R  S

48. A compound according to claim 41 wherein $R_2'$ is

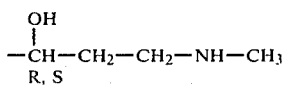
R, S

49. A compound according to claim 41 wherein $R_2'$ is

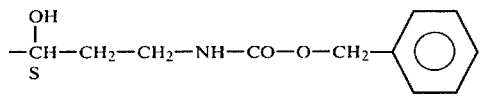

50. A compound according to claim 41 wherein $R_2'$ is

—CH—CH$_2$—NH—CH$_3$.
  |
  OH
  S

51. A compound according to claim 41 wherein $R_2'$ is

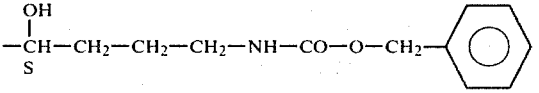

* * * * *

UNITED STATES PATENT AND TRADEMARK OFFICE
CERTIFICATE OF CORRECTION

PATENT NO. : 4,220,755

DATED : September 2, 1980

INVENTOR(S) : MORIYUKI SATO, et al.

It is certified that error appears in the above-identified patent and that said Letters Patent are hereby corrected as shown below:

Col. 2, line 61, "49,15" should be --49.15--;

Col. 9, Table 3-1; Under Strain Name; line 3, "a ureus" should be --aureus--;

line 5, "Eschericihia" should be --Escherichia--;

line 6, "Eschericihia" should be --Escherichia--;

Col. 10, Table 2, line 10, Compound 38, "hydroxybutyl" should be --hydroxybutyryl--;

Col. 11, Table 3-2, Compound No. 33, the entries should read:

--0.32     0.32     1.25     2.5     5     1.25     10--;

Col. 12, line 38, "(VI)" should be --(VII)--;

Col. 19, line 13 "(IV)" should be --(V)--;

Col. 27, line 23 "ractions" should be --reactions--;

UNITED STATES PATENT AND TRADEMARK OFFICE
CERTIFICATE OF CORRECTION

PATENT NO. : 4,220,755

DATED : September 2, 1980

INVENTOR(S) : MORIYUKI SATO, et al.

It is certified that error appears in the above-identified patent and that said Letters Patent are hereby corrected as shown below:

Col. 30, in Table D, after "21-3", "4-N-(n-butyryl)fportimicin B" should be --4-N-(n-butyryl)fortimicin B--;

Col. 32, line 28 "[60]" should be --[$\alpha$]--;

Col. 40, Claim 8, line 9, "$-CH_2-CH_2-CH_2-CH_2-NH_2$" should be -- $-CH_2-CH_2-CH_2-CH_2-CH_2-NH_2$ --

Signed and Sealed this

Tenth Day of February 1981

[SEAL]

Attest:

RENE D. TEGTMEYER

Attesting Officer

Acting Commissioner of Patents and Trademarks